United States Patent
Son et al.

(10) Patent No.: US 9,745,555 B2
(45) Date of Patent: Aug. 29, 2017

(54) BACTERIOPHAGE AND ANTIBACTERIAL COMPOSITION COMPRISING THE SAME

(71) Applicant: CJ CHEILJEDANG CORPORATION, Seoul (KR)

(72) Inventors: Bo Kyung Son, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 49 days.

(21) Appl. No.: 14/767,269

(22) PCT Filed: Feb. 26, 2014

(86) PCT No.: PCT/KR2014/001592
§ 371 (c)(1),
(2) Date: Aug. 11, 2015

(87) PCT Pub. No.: WO2014/133323
PCT Pub. Date: Sep. 4, 2014

(65) Prior Publication Data
US 2016/0076004 A1    Mar. 17, 2016

(30) Foreign Application Priority Data
Feb. 27, 2013    (KR) .................. 10-2013-0021499

(51) Int. Cl.
*C12N 7/00*    (2006.01)
*A61K 35/76*    (2015.01)

(52) U.S. Cl.
CPC ............... *C12N 7/00* (2013.01); *A61K 35/76* (2013.01); *C12N 2795/10321* (2013.01); *C12N 2795/10331* (2013.01); *C12N 2795/10332* (2013.01)

(58) Field of Classification Search
None
See application file for complete search history.

(56) References Cited

U.S. PATENT DOCUMENTS

| 7,625,739 B2 | 12/2009 | Pasternack et al. |
| 7,625,740 B2 | 12/2009 | Pasternack et al. |
| 2009/0047727 A1 | 2/2009 | Pasternack et al. |

FOREIGN PATENT DOCUMENTS

| CN | 102317431 A | 1/2012 |
| EP | 2143729 A1 | 1/2010 |
| JP | 2011-527188 A | 10/2011 |
| KR | 10-2009-0021475 A | 3/2009 |
| KR | 10-0910961 B1 | 8/2009 |
| KR | 10-2012-0076710 A | 7/2012 |

OTHER PUBLICATIONS

Miller et al., "Bacteriophage Therapy for Control of Necrotic Enteritis of Broiler Chickens Experimentally Infected with Clostridium perfringens", Avian Diseases, 2010, vol. 54, No. 1, pp. 33-40.
International Search Report dated May 9, 2014 of PCT/KR2014/001592 which is the parent application—4 pages.
Office Action dated Sep. 12, 2016 of corresponding Chinese Application No. 201480010715.3—7 pages.
English Abstract of Cislo M, et al., "Archivum Immunologiae et Therapiae Experimentalis", Ther. Exp. 2:175-183, 1987.
Zimmer et al., "Genomic Analysis of Clostridium perfringens Bacteriophage Φ3626, Which Integrates into guaA and Possibly Affects Sporulation", Journal of Bacteriology, Aug. 2002, vol. 184, No. 16, pp. 4359-4368.
Nariya et al., "Identification and characterization of a putative endolysin encoded by episomal phage phiSM101 of Clostridium perfringens", Applied Microbiology and Biotechnology, 2011, vol. 90, pp. 1973-1979.
Zimmer et al., "The Murein Hydrolase of the Bacteriophage Φ3636 Dual Lysis System is Active against All Tested Clostridium perfringens Strains", Applied and Environmental Microbiology, Nov. 2002, vol. 68, No. 11, pp. 5311-5317.
Sung Hoon Kim et al., "Bacteriophage, New Alternative Antibiotics", BioWave; Biological Research Information Center, BRIC, 2005, vol. 7, No. 15—10 pages.
Hermoso et al., "Taking aim on bacterial pathogens: from phage therapy to enzybiotics", Current Opinion in Microbiology, 2007, vol. 10, pp. 461-472.
Kim et al., "Inducible Clostridium perfringens bacteriophages ΦS9 and ΦS63", Bacteriophage, Apr./May/Jun. 2012, vol. 2, No. 2, pp. 89-97.
Office Action dated Aug. 9, 2016 of corresponding Japanese Patent Application No. 2015-560097—4 pages.
Extended European Search Report dated Jun. 30, 2016 of European Patent Application No. 14757580.7—6 pages.

*Primary Examiner* — Michelle S Horning
(74) *Attorney, Agent, or Firm* — Knobbe Martens Olson & Bear LLP

(57) ABSTRACT

Provided is a novel bacteriophage ΦCJ21 (KCCM11363P). In addition, the present invention relates to an antibacterial composition including the bacteriophage ΦCJ21 (KCCM11363P) as an active ingredient. Further, provided is a method of preventing and/or treating infectious diseases by *Clostridium perfringens* in animals except for humans using the bacteriophage ΦCJ21 (KCCM11363P) or the antibacterial composition containing the bacteriophage ΦCJ21 (KCCM11363P) as an active ingredient.

8 Claims, 3 Drawing Sheets

BACTERIOPHAGE AND ANTIBACTERIAL COMPOSITION COMPRISING THE SAME

CROSS REFERENCE TO RELATED APPLICATIONS

This application is the U.S. National Phase Application under 35 U.S.C. §371 of International Application No. PCT/KR2014/001592, filed Feb. 26, 2014, designating the U.S. and published as WO 2014/133323 A1 on Sep. 4, 2014 which claims the benefit of Korean Patent Application No. KR-10-2013-0021499, filed Feb. 27, 2013. Any and all applications for which a foreign and/or a domestic priority is claimed is/are identified in the Application Data Sheet filed herewith and is/are hereby incorporated by reference in their entirety under 37 C.F.R. §1.57.

REFERENCE TO SEQUENCE LISTING

This application incorporates by reference the sequence listing submitted as ASCII text filed via EFS-Web on Aug. 11, 2015, and updated by a file entitled "AIP22.011APC_REPLACEMENT_SEQLIST.txt" which is 62,240 bytes in size, created on Nov. 19, 2015, and last modified on Nov. 23, 2015.

TECHNICAL FIELD

The present invention relates to a novel bacteriophage having a specific bactericidal activity against pathogenic *Clostridium perfringens* and an antibacterial composition comprising the same. In addition, the present invention relates to a method of preventing or treating animal diseases using the novel bacteriophage or the antibacterial composition.

BACKGROUND ART

*Clostridium perfringens* (CP), which is gram-positive large obligatory anaerobic *bacillus*, has been known as a bacterium that does not have flagellum and forms a spore. *Clostridium perfringens*, which is a bacterium causing diarrhea, or the like, particularly, in domestic animals such as chicken, pig, etc., and the like, has been recognized as one of the important and fatal pathogenic bacteria in a livestock industry, as well as *Salmonella* causing fowl typhoid.

Currently, one of the diseases frequently generated in poultry and pork industries is Necrotic Enteritis by *Clostridium perfringens*. It is known that Necrotic Enteritis is frequently generated by co-infection of *Clostridium perfringens* and Coccidium, and as a main symptom of necrotic enteritis, there is bloody diarrhea due to severe necrotic lesions in a lower portion of small intestine of chickens, swines, or the like.

This necrotic enteritis generates dehydration symptom, periodic diarrhea, and the like, in an infected animal according to the disease severity, gradually debilitates a body of the animal, and causes growth retardation, and the like, such that necrotic enteritis has become a significant problem in the livestock industry. Further, since *Clostridium perfringens* is easily propagated through feces of animal, transmission between animals in a common breeding space may be easily generated by oral infection through soil or contaminated feed, or the like. Particularly, incidence in young animal is high, such that *Clostridium perfringens* has become a problem.

Meanwhile, bacteriophage is a specialized type of virus that infects and destroys only bacteria, and can self-replicate only inside host bacteria. The bacteriophage has strong host specificity as compared to antibiotics, and recently, a problem of emergence of strain resistant against antibiotics has become serious, such that an interest in practical use of the bacteriophage has increased (Non-Patent Documents 1 and 2).

Therefore, research concerning the bacteriophage has been actively conducted in various countries around the world, and in addition to a patent application for bacteriophage, an attempt to acquire Food and Drug Administration (FDA) approval for a composition containing the bacteriophage has been gradually increased.

As the prior art documents concerning the bacteriophage, a bacteriophage having a specific bactericidal activity against *Clostridium perfringens* has been disclosed in Patent Document 1, and a bacteriophage having a specific bactericidal activity against *Staphylococcus aureus* has been disclosed in Patent Document 2. Further, lytic protein derived from a bacteriophage specifically destroying peptidoglycan structure of bacterial cell membrane, and bacteria lysates by the lytic protein have been disclosed in Patent Document 3.

However, in spite of presence of the following prior arts, a technology associated with the bacteriophage for preventing and/or treating infectious diseases, particularly, necrotic enteritis by *Clostridium perfringens* that is a still important problem in the livestock industry including poultry and pork industries is still insufficient, such that a bacteriophage and a technology associated with the bacteriophage should be developed.

PRIOR ART DOCUMENT

Patent Document (Patent Document 1) Korean Patent Laid-open Publication No. 10-2012-0076710 A
(Patent Document 2) Korea Patent Registration No. 10-0910961 B1
(Patent Document 3) Korean Patent Laid-Open Publication No. 10-2009-0021475 A

Non-Patent Document (Non Patent Document 1) Cislo M, et al., Arch. Immunol. Ther. Exp. 2:175-183, 1987
(Non Patent Document 2) Sung Hoon Kim et al, Bacteriophage, novel alternative antibiotics, BioWave Vol. 7 No. 15, 2005, BRIC

DISCLOSURE

Technical Problem

The present inventors conducted studies in order to solve problems such as resistant bacteria occurring upon the use of antibiotics, antibiotics remaining in meat, and the like, and efficiently prevent and treat infectious diseases by *Clostridium perfringens*, and as a result, the present inventors isolated new bacteriophage ΦCJ21 (KCCM11363P) having a specific bactericidal activity against *Clostridium perfringens* from the nature.

In addition, the present inventors identified morphological, biochemical, and genetic characteristics of the novel bacteriophage and confirmed that the bacteriophage had excellent acid resistance, heat resistance, drought resistance, and the like, thereby developing an antibiotic, a disinfectant, a feed additive, and other compositions using the novel bacteriophage. Further, the present inventors developed a composition for preventing or treating infectious diseases by *Clostridium perfringens* and a method of preventing or treating the disease using the composition.

The present invention intends to provide a novel bacteriophage ΦCJ21 (KCCM11363P) having a specific bactericidal activity against *Clostridium perfringens*.

In addition, the present invention intends to provide a composition for preventing and/or treating infectious diseases by *Clostridium perfringens* containing the bacteriophage ΦCJ21 (KCCM11363P) as an active ingredient.

Further, the present invention intends to provide an antibiotic, a feed additive, a drinking water additive, a disinfectant, or a cleaner containing the bacteriophage ΦCJ21 (KCCM11363P) as an active ingredient.

Furthermore, the present invention intends to provide a method of preventing and/or treating infectious diseases by *Clostridium perfringens* in animals except for humans using the bacteriophage ΦCJ21 (KCCM11363P) or a composition containing the same (KCCM11363P) as an active ingredient.

Technical Solution

According to an exemplary embodiment of the present invention, there is provided a novel bacteriophage ΦCJ21 (KCCM11363P) having a specific bactericidal activity against *Clostridium perfringens*.

According to another exemplary embodiment of the present invention, there is provided a composition for preventing or treating an infectious disease caused by *Clostridium perfringens*, the composition containing the bacteriophage ΦCJ21 (KCCM11363P) as described above as an active ingredient.

According to another exemplary embodiment of the present invention, there are provided an antibiotic, a feed additive, a drinking water additive, a disinfectant or a cleaner containing the bacteriophage ΦCJ21 (KCCM11363P) as described above as an active ingredient.

According to another exemplary embodiment of the present invention, there is provided a method of preventing or treating an infectious disease caused by *Clostridium perfringens*, comprising administering the bacteriophage ΦCJ21 (KCCM11363P) or the composition containing the same as described above to animals except for humans.

Advantageous Effects

The bacteriophage ΦCJ21 (KCCM11363P) according to the present invention has an effect of specifically killing *Clostridium perfringens*.

In addition, the bacteriophage ΦCJ21 (KCCM11363P) according to the present invention has excellent acid resistance, heat resistance, and drought resistance, such that the bacteriophage ΦCJ21 (KCCM11363P) may be used as a material for preventing or treating infectious diseases by *Clostridium perfringens* in various temperature or pH ranges, moisture conditions, and the like, and utilized as an antibiotic, a feed additive, a drinking water additive, a disinfectant, a cleaner, or the like.

Further, according to the present invention, infectious diseases caused by *Clostridium perfringens* may be prevented or treated by administering the bacteriophage ΦCJ21 (KCCM11363P) or a composition containing the same (KCCM11363P) as an active ingredient to animals except for human.

BEST MODE

Hereinafter, the present invention will be described in detail. Since contents that are not described in the present specification may be sufficiently recognized and inferred by those skilled in the art or similar art, a description thereof will be omitted.

In one embodiment, the present invention provides a novel bacteriophage ΦCJ21 (KCCM11363P) having a specific bactericidal activity against *Clostridium perfringens* (CP).

It is known that *Clostridium perfringens*, which is gram-positive large obligatory anaerobic *bacillus*, does not have a flagellum and forms a spore. *Clostridium perfringens*, which is a bacterium causing diarrhea, or the like, in animals, particularly, in domestic animals such as poultry, swine, and the like, has been recognized as one of the dangerous and fatal pathogenic bacteria in a livestock industry such as *Salmonella* causing fowl typhoid.

A bacteriophage is a bacteria-specific virus infecting specific bacteria to suppress and inhibit growth of the bacteria, and means a virus including single or double stranded deoxyribonucleic acid (DNA) or ribonucleic acid (RNA) as a genetic material.

Figure 1:
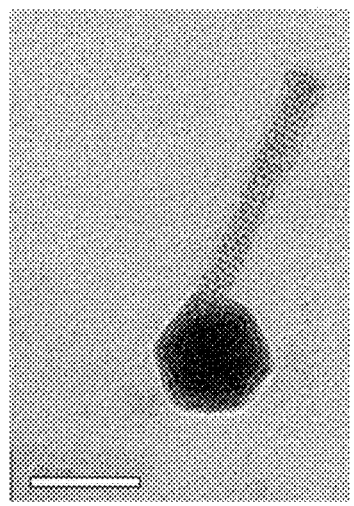
FIG. 1 is an electron microscope photograph of a novel bacteriophage ΦCJ21 (KCCM11363P, hereinafter, referred to as 'ΦCJ21').

A bacteriophage ΦCJ21 of the present invention, which is a bacteriophage having species-specificity of selectively infecting *Clostridium perfringens* has an isometric capsid and a non-contractile tail, and morphologically belongs to Siphoviridae (FIG. 1). Homology analysis data of nucleic acid sequences between bacteriophage ΦCJ21 and other bacteriophages is shown in table 1. Activity of bacteriophage ΦCJ21 was stable at the range from pH 4 to pH 9.8 (acid resistance, see FIG. 4). ΦCJ21 retained its activity for 2 hours when it was exposed at 60° C. (heat resistance, see FIG. 5), and its titer was decreased about 1/10 after drying (see FIG. 6). The nucleic acid sequence of bacteriophage ΦCJ21 is the same as SEQ ID NO: 1.

The bacteriophage ΦCJ21, which was a bacteriophage newly isolated by the present inventors, was deposited at Korean Culture Center of Microorganisms (361-221, Hongjedong, Seodaemun-gu, Seoul, Korea) as a deposition number KCCM11363P on Jan. 30, 2013.

In another embodiment, the present invention provides a composition for preventing or treating infectious diseases by *Clostridium perfringens* containing the bacteriophage ΦCJ21 as an active ingredient. As a preferable example of the composition, the present invention provides an antibiotic.

Since the bacteriophage ΦCJ21 has an antibacterial activity capable of specifically killing *Clostridium perfringens*, the bacteriophage ΦCJ21 may be used to prevent or treat diseases generated by infection of *Clostridium perfringens*. As a suitable example of the infectious disease caused by *Clostridium perfringens* capable of being treated using the bacteriophage ΦCJ21, there is Necrotic Enteritis, but the present invention is not limited thereto.

Necrotic Enteritis, which is one of the main infectious diseases caused by *Clostridium perfringens*, corresponds to a bacterial disease most frequently generated in domestic animals, particularly, poultry and causes significant damage. The disease may be generated in poultry, especially chickens substantially at all ages, but is mainly generated in chickens (2 to 5 weeks old) bred on the floor and also frequently generated in chickens (12 to 16 weeks old) bred in a cage.

As *Clostridium perfringens* is excessively proliferated in the small intestine, symptoms of Necrotic Enteritis are generated, and necrosis of gastrointestinal mucosa, sudden diarrhea, and the like, are caused. For example, in swines, in the case of very acute necrotic enteritis, after 1 to 2 days of occurrence, mortality of the swine is generated, and in the case of acute necrotic enteritis, after 2 to 3 days of bloody diarrhea, mortality of the swine is generated. Further, in the case of sub-acute necrotic enteritis, diarrhea (there is no bloody feces) proceeds for 5 to 7 days, and then weakness and dehydration are caused, and in the case of chronic necrotic enteritis, intermittent diarrhea is caused, and growth disorder may be generated.

The term "prevention" as used herein refers to all actions of providing the bacteriophage ΦCJ21 and/or the composition containing the same as the active ingredient to animals except for humans to suppress the corresponding disease or retard disease occurring.

The term "treatment" as used herein refers to all actions of providing the bacteriophage ΦCJ21 and/or the composition containing the same as the active ingredient to animals, except for humans, to thereby allow the symptom of the corresponding disease caused by infection to get better or be alleviated.

As an example of the infectious disease caused by *Clostridium perfringens* to which the bacteriophage ΦCJ21 and/or the composition containing the same as the active ingredient may be applied, there is necrotic enteritis, but the present invention is not limited thereto.

The composition for preventing or treating the infectious diseases caused by *Clostridium perfringens* according to the present invention may contain the bacteriophage ΦCJ21 at a content of preferably $5 \times 10^6$ to $5 \times 10^{12}$ pfu/ml, more preferably, $1 \times 10^6$ to $1 \times 10^{10}$ pfu/ml.

The composition for preventing or treating infectious diseases caused by *Clostridium perfringens* according to the present invention may further contain a pharmaceutically acceptable carrier, and be formulated together with the carrier to thereby be provided as food, a drug, a feed additive, a drinking water additive, and the like. The term "Pharmaceutically acceptable carrier" as used herein means a carrier or a diluent that does not stimulate living organism nor inhibit biological activity and properties of an administered compound.

A kind of carrier usable in the present invention is not particularly limited, and any carrier may be used as long as it is generally used in the art and is pharmaceutically acceptable. As a non-restrictive example of the carrier, there are saline, sterile water, Ringer's solution, buffered saline, an albumin injection solution, a dextrose solution, a maltodextrin solution, glycerol, ethanol, and the like. These can be used alone or as a mixture of at least two of these.

In addition, if necessary, another general additive such as an antioxidant, a buffer, and/or a bacteriostatic agent, etc., may be further added and used, and the composition may be formulated into an injection formulation such as an aqueous solution, suspension, emulsion, or the like, pills, capsules, granules, tablets, or the like by additionally adding a diluent, a dispersant, a surfactant, a binder, and/or a lubricant, etc., and then used.

An administration method of the composition for preventing or treating infectious diseases by *Clostridium perfringens* is not particularly limited, but any method generally used in the art may be used. As a non-restrictive example of the administration method, the composition may be orally or parenterally administered.

As a non-restrictive example of the formulation for oral administration, there are troches, lozenge, tablets, aqueous suspensions, oily suspensions, prepared powder, granules, emulsions, hard capsules, soft capsules, syrups, elixirs, or the like.

In order to formulate the composition according to the present invention into a formulation such as a tablet, a capsule, or the like, the formulation may further contain a binder such as lactose, saccharose, sorbitol, mannitol, starch, amylopectin, cellulose, gelatin; an excipient such as dicalcium phosphate, or the like; a disintegrant such as corn starch, sweet potato starch, or the like; a lubricant such as magnesium stearate, calcium stearate, sodium stearyl fumarate, polyethylene glycol wax, or the like. In the case of the capsule formulation, the formulation may additionally contain a liquid carrier such as fatty oil in addition to the above-mentioned materials.

As a parenteral administration method, an intravenous administration method, an intraperitoneal administration method, an intramuscular administration method, a subcutaneous administration method, or a local administration method, etc., may be used. In addition, a method of applying or spraying the composition onto a disease site may also be used, but the present invention is not limited thereto.

An example of the formulation for parenteral administration may include injection formulations for subcutaneous injection, intravenous injection, intramuscular injection, or the like; suppository formulations; spray formulations such as aerosol formulations capable of being inhaled through respiratory system, or the like, but the present invention is not limited thereto. In order to formulate the composition into the injection formulation, the composition according to the present invention may be mixed with a stabilizer or a buffer in water to thereby prepare a solution or suspension, and then, the prepared solution or suspension may be formulated in a unit dose for an ampoule or vial. In the case of formulating the composition into the spray formulation such as the aerosol formulation, or the like, a propellant, or the like, may be mixed together with an additive so that a water-dispersed condensate or wet powder is dispersed.

A suitable application, spray, or administration dose of the composition for preventing or treating infectious diseases by *Clostridium perfringens* may be variously determined depending on factors such as age, weight, sex, degree of symptom of disease, a kind of food, excretion rate of administration subject animals, or the like, as well as a method of formulating the composition, an administration method, an administration time and/or route. Generally, a veterinarian having ordinary skill in the art may easily determine and prescribe an effective dose for the desired treatment.

In another embodiment, the present invention may provide an antibiotic containing the bacteriophage ΦCJ21 as an active ingredient.

The term "antibiotic" as used herein means an agent capable of being provided to animals including humans in a drug form to thereby kill bacteria, and corresponds to a concept collectively indicating a preservative, a disinfectant, and an antibacterial agent.

The antibiotic containing the bacteriophage ΦCJ21 according to the present invention as the active ingredient may have high specificity to *Clostridium perfringens* as compared to an antibiotic according to the prior art to thereby not kill beneficial bacteria but kill specific pathogenic bacteria, and does not induce drug resistance, such that the antibiotic according to the present invention may be provided as a novel antibiotic having an elongated lifespan as compared to the antibiotic according to the prior art.

In another embodiment, the present invention may provide a feed additive and a drinking water additive containing the bacteriophage ΦCJ21 as an active ingredient.

The feed additive and the drinking water additive according to the present invention may be used in a manner in which the bacteriophage ΦCJ21 or the composition containing the smae is individually prepared in a feed additive or drinking water additive form and then mixed with a feed or drinking water, or in a manner in which the bacteriophage ΦCJ21 or the composition containing the same is directly added at the time of preparing the feed or the drinking water.

The bacteriophage ΦCJ21 or the composition containing the same used as the feed additive or drinking water additive according to the present invention may be in a liquid state or dried state, and preferably, in a dried powder form.

A drying method for preparing the feed additive and the drinking water additive according to the present invention in the dried powder form is not particularly limited, but a method generally used in the art may be used. As a non-restrictive example of the drying method, there is air drying method, natural drying method, a spray drying method, a freeze-drying method, or the like. One method of these methods may be used alone or at least two methods may be used together with each other.

Another non-pathogenic microbe may be additionally added to the feed additive or drinking water additive. A non-restrictive example of the microbe capable of being added may be selected from a group consisting of *bacillus subtilis* capable of producing protease, lipase, and/or sugar converting enzyme such as *bacillus subtilis*, or the like; *Lactobacillus* sp. having physiological activity and degradation activity for an organic material under anaerobic conditions such as stomach of cow; mold fungi having effects of increasing a weight of domestic animal, a milk yield, and digestibility of the feed such as *Aspergillus oryzae*, or the like; and yeasts such as *Saccharomyces cerevisiae*, or the like. These can be used alone or as a mixture of at least two of these.

The feed additive or the drinking water additive containing the bacteriophage ΦCJ21 according to the present invention as the active ingredient may further contain other additives, as needed. As a non-restrictive example of the usable additive, there are a binder, an emulsifier, a preservative, and the like, which are added in order to prevent quality of the feed or driving water from being deteriorated; amino acids, vitamins, enzymes, probiotics, flavoring agents, non-protein nitrogen compounds, silicates, buffers, coloring agents, extractants, oligosaccharides, and the like, which are added in order to increase utility of the feed or drinking water. Otherwise, the additive may further include a feed mixing agent, or the like. These can be used alone or as a mixture of at least two of these.

The feed additive may be contained at a content of 0.05 to 10, more preferably 0.1 to 2 parts by weight based on 100 parts by weight of the feed. The drinking water additive may be contained at a content of 0.0001 to 0.01, more preferably 0.001 to 0.005 parts by weight based on 100 parts by weight of the drinking water. The activity of the bacteriophage ΦCJ21 against *Clostridium perfringens* may be sufficiently exhibited in the above-mentioned range.

In another embodiment the present invention provides a feed or drinking water prepared by adding a feed additive or a drinking water additive containing the same as an active ingredient or directly adding the bacteriophage ΦCJ21.

The feed used in the present invention is not particularly limited, but any feed generally used in the art may be used. A non-restrictive example of the feed may include plant feeds such as grains, roots and fruit, food processing byproducts, algaes, fiber, pharmaceutical byproducts, fats, starches, cucurbitaceous, or grain byproducts; and animal feeds such as proteins, inorganic materials, fats, minerals, single cell proteins, animal planktons, or foods. These can be used alone or as a mixture of at least two of these.

The drinking water used in the present invention is not particularly limited, but any drinking water generally used in the present invention may be used.

In another embodiment, the present invention may provide a disinfectant or a cleaner containing the bacteriophage ΦCJ21 as an active ingredient. A formulation of the disinfectant or cleaner is not particularly limited, but the disinfectant or cleaner may be formulated into any formulation known in the art.

The disinfectant may be sprayed in order to remove *Clostridium perfringens* onto a region in which animals live, a slaughterhouse, a mortality rea, a cooking place or cooking equipment, or the like, but the present invention is not limited thereto.

The cleaner may be used to wash surfaces of the skin or each of the sites of bodies of animals, particularly, poultry or swines, exposed or to be exposed to *Clostridium perfringens*, but the present invention is not limited thereto.

In another embodiment, the present invention provides a method of preventing or treating infectious diseases caused by *Clostridium perfringens* by using the bacteriophage ΦCJ21 or the composition containing the same as an active ingredient. The infectious disease may be preferably necrotic enteritis, but the present invention is not limited thereto. The target of preventing or treating infectious disease caused by *Clostridium perfringens* may be a poultry or swine, but the present invention is not limited thereto.

In detail, the method of preventing or treating infectious diseases according to the present invention may include administering the bacteriophage ΦCJ21 or the composition containing the same as the active ingredient to targets infected by *Clostridium perfringens* or being at risk of infection of *Clostridium perfringens* except for humans in a pharmaceutically effective dose. It will be apparent to those skilled in the art that when the pharmaceutical composition is administered to patient, the suitable total daily dose may be determined by an attending physician or veterinarian within the scope of sound medical judgement.

A specific pharmaceutically effective dose of the bacteriophage ΦCJ21 or the composition containing the same as the active ingredient for a specific animal may be determined by considering an administration time and an administration route of the bacteriophage ΦCJ21 or the composition containing the same, a secretion rate of the composition, a therapy duration period, or the like, in addition to a kind and a degree of the desired response, an age, a weight, a general healthy state, sex, or diet of the corresponding individual. In addition, the pharmaceutically effective dose may be variously changed according to various factors such as ingredients of drugs or other compositions simultaneously or separately used and similar factors well known in a medical field.

The bacteriophage ΦCJ21 according to the present invention or the composition containing the same as the active ingredient may be administered as a pharmaceutical form (nasal spray) to animals or administered in a method of directly added to a feed or drinking water of the animals and then feeding the feed or drinking water. In addition, the bacteriophage ΦCJ21 or the composition containing the same may be mixed in a feed or drinking water in a form of a feed additive or drinking water additive and then administered.

The administration route and administration method of the bacteriophage ΦCJ21 according to the present invention or the composition containing the same as the active ingredient are not particularly limited, but any administration route and administration method may be used as long as the bacteriophage ΦCJ21 or the composition containing the same may arrive at the corresponding target tissue. That is, the bacteriophage ΦCJ21 or the composition containing the same as the active ingredient may be administered through various oral or parenteral routes. As a non-restrictive example of the administration route, oral, rectal, local, intravenous, intraperitoneal, intramuscular, intraarterial, subcutaneous, and nasal administration, or inhalation, etc., may be performed.

Hereinafter, the present invention will be described in detail through the Examples. However, these Examples are only to illustrate the present invention, and a scope of the present invention is not limited to these Examples.

Example 1 Isolation of Bacteriophage Infecting
*Clostridium perfringens*

Examples 1-1

Screening of Bacteriophage and Isolation of Single Bacteriophage

After 50 ml of a sample isolated from a feces sample of Samwhaw Gps. Breeding Agri. Inc., which is a chicken and pig farm in South Chungchong Province, was moved a centrifuge bottle and centrifuged at 4,000 rpm for 10 minutes, the supernatant was filtered with a 0.45 μm filter to prepare a sample solution, and then a soft agar overlay method was performed using the prepared sample solution. The soft agar overlay method is a method of observing a lysis action of bacteriophage using host cells growing in top agar (attached onto a solid medium using 0.7% agar).

In detail, 18 ml of sample filtrates was mixed with 150 μl of a shake culture solution ($OD_{600}$=2) of *Clostridium perfringens*, (CP, BCCP 17-1) isolated at Animal and Plant Quarantine Agency and 2 ml of 10× Brain-heart infusion (hereinafter, 'BHI' medium) (composed so as to have a final volume of 1 L) and cultured at 37° C. for 18 hours. Then, the culture solution was centrifuged at 4,000 rpm for 10 minutes, and the supernatant was filtered using the 0.45 μm filter. Thereafter, after a mixture of 5 ml of 0.7% agar (w/v) and 150 μl of the shake culture solution ($OD_{600}$=2) of *Clostridium perfringens* (BCCP 17-1) was poured and hardened into a BHI plate (BHI+0.2% sheep blood), 10 μl of the sample culture filtrate solution was dropped thereon, followed by culturing at 30° C. for 18 hours. Then, it was confirmed that a plaque was formed.

After the sample culture filtrate solution in which lysis was generated was appropriately diluted and mixed with 150 μl of the shake culture solution ($OD_{600}$=2) of *Clostridium perfringens* (BCCP 17-1), the soft agar overlay method was performed, thereby obtaining a single plaque. Since it is considered that a single plaque is formed of a single bacteriophage, in order to purify and isolate the single bacteriophage, a single plaque was selected, put into 400 μl of a SM solution (NaCl 5.8 g/l; MgSO47H2O 2 g/l; 1 M Tris-Cl (pH 7.5), 50 ml; H2O, composed so as to have a final volume of 1 L), and left at room temperature for 4 hours, thereby purifying and isolating the single bacteriophage.

In order to secure a large amount of the isolated bacteriophage, 100 μl of a supernatant of a single bacteriophage solution was selected and mixed with 120 of 0.7% agar and 500 of the shake culture solution of *Clostridium perfringens* (BCCP 17-1), followed by performing the soft agar overlay method in a LB medium having a diameter of 150 mm. After pouring 15 ml of the SM solution into a plate in which lysis was completely generated, the plate was softly shaken at room temperature for 4 hours, thereby discharging the bacteriophage in the top-agar. The SM solution in which the bacteriophage was discharged was recovered, and chloroform was added thereto at an amount of 1% of the final volume and suitably mixed for 10 minutes, followed by centrifugation at 4,000 rpm for 10 minutes. The supernatant obtained as described above was filtered with a 0.45 μm filter and stored at a cold temperature.

Examples 1-2

Large Scale Culture and Purification of Bacteriophage

The selected bacteriophage was cultured at large scale using *Clostridium perfringens* (BCCP 17-1), and then the bacteriophage was purified therefrom.

In detail, 1% of the shake culture solution of *Clostridium perfringens* (BCCP 17-1) was inoculated into a liquid culture medium for mass production, and at the same time, the bacteriophage was put thereinto at multiplicity of infection (MOI) of 0.1, simultaneously with the inoculation of *Clostridium perfringens* (BCCP 17-1), thereby performing co-infection. Then, static culture was performed at 30° C. under anaerobic conditions.

Thereafter, centrifugation was performed at 4° C. and 12,000 rpm for 20 minutes, and then the supernatant was filtered with a 0.45 μm filter. After NaCl and polyethylene glycol (PEG) were added to the filtered supernatant so as to have final concentrations of 1M and 10% (w/v), respectively, and mixed with each other, the mixture was further left at 4° C. for 8 hours or more. Next, after centrifugation was performed at 4° C. and 12,000 rpm for 20 minutes, then the supernatant was removed, and the precipitates were obtained.

The obtained precipitate was resuspended using 5 ml of the SM solution and was left at room temperature for 20 minutes. Thereafter, the supernatant was filtered with a 0.45 μm filter, and ultracentrifugation (35,000 rpm, 1 hour, 4° C.) using a glycerol density gradient method (density: 40%, 5% glycerol) was performed, thereby purifying the bacteriophage ΦCJ21. After the purified ΦCJ21 was resuspended using 500 μl of the SM solution, a titer was measured.

The present inventor called the bacteriophage obtained by extracting the sample from feces and having the specific bacteriocidal activity against *Clostridium perfringens* "Bacteriophage ΦCJ21" and deposited the bacteriophage at Korean Culture Center of Microorganisms (361-221, Hongjedong, Seodaemun-gu, Seoul, Korea) as a deposition number KCCM11363P on Jan. 30, 2013.

Example 2

Morphology Observation of ΦCJ21

The purified bacteriophage ΦCJ21 was diluted in 0.01% gelatin solution and then fixed by 2.5% glutaraldehyde solution. The fixed bacteriophage was dropped onto a carbon-coated mica plate (ca. 2.5 mm×2.5 mm), adapted thereto for 10 minutes, and washed with sterile distilled water. A carbon film was mounted on a copper grid, stained with 4% uranyl acetate for 30 to 60 seconds, dried, and investigated using a transmission electron microscope (JEM-1011, 80 kV, magnification: X120,000 to X200,000) (FIG. 1).

FIG. 1 shows an electron microscope photograph of the bacteriophage ΦCJ21, and it may be appreciated that since the bacteriophage does not have an isometric capsid and a contractile tail, the bacteriophage morphologically belongs to Siphoviridae.

Example 3

Genomic DNA Size Analysis of ΦCJ21

Genomic DNA was extracted from the bacteriophage ΦCJ21 purified by the ultracentrifugation. In detail, ethylenediaminetetraacetic acid (EDTA, pH 8.0), proteinase K, and sodium dodecyl sulfate (SDS) were added to a culture solution of the purified bacteriophage ΦCJ21 so as to have final concentrations of 20 mM, 50 μg/ml, and 0.5% (w/v), respectively, and then, were in a stationary state at 50° C. for 1 hour. Thereafter, an equal volume of phenol (pH 8.0) was added thereto and stirred, followed by centrifugation at room temperature and 12,000 rpm for 10 minutes, thereby obtaining a supernatant.

The supernatant was mixed with an equal volume of PC (phenol:chloroform=1:1) and centrifuged at room temperature and 12,000 rpm for 10 minutes, thereby obtaining a supernatant. The supernatant was mixed with an equal volume of chloroform and centrifuged at room temperature and 12,000 rpm for 10 minutes, thereby obtaining a supernatant. The obtained supernatant was sequentially mixed with 10% (v/v) of 3M sodium acetate and a double volume of cold 95% ethanol, based on the total volume, and left at −20° C. for 1 hour. Subsequently, centrifugation was performed at 0° C. and 12,000 rpm for 10 minutes, and the precipitate was obtained by removing the supernatant. Then, 50 μl of Tris-EDTA (TE) buffer (pH 8.0) was added thereto to thereby dissolve the obtained precipitate. The extracted DNA was diluted 10 times, and a concentration was measured by measuring absorbance at $OD_{260}$.

Figure 2:
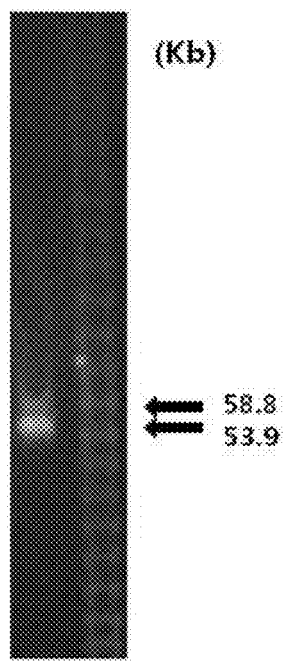
FIG. 2 shows a pulsed field gel electrophoresis (PFGE) result of the novel bacteriophage ΦCJ21.

Next, 1 μg of DNA was loaded onto 1% pulse-field gel electrophoresis (PFGE) agarose gel, and electrophoresis was performed at room temperature for 20 hours using a BIO-RAD PFGE system program 7 (size range: 25-100 kb; switch time ramp: 0.4-2.0 seconds, linear shape; forward voltage: 180 V; reverse voltage: 120 V) (FIG. 2).

FIG. 2 is a pulsed field gel electrophoresis (PFGE) photograph of the genomic DNA of the bacteriophage ΦCJ21, and it may be confirmed that the genomic DNA of the bacteriophage ΦCJ21 has a size of about 56 kb.

Example 4

Protein Pattern Analysis of ΦCJ21

15 μl of purified bacteriophage ΦCJ21 solution ($10^{10}$ pfu/ml titer) was mixed with 3 μl of a 5× SDS sample solution, and heated for 5 minutes. Thereafter, the total protein of the bacteriophage ΦCJ21 was expanded in 15% SDS-PAGE gel, and then the gel was stained at room temperature for 1 hour using a coomassie blue dye solution (FIG. 3).

Figure 3:
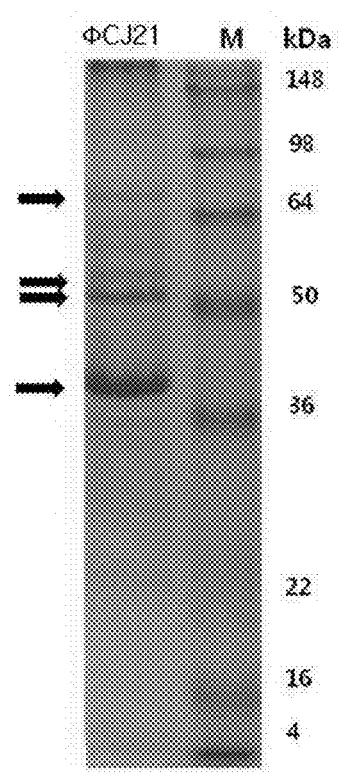
FIG. 3 shows a sodiumdodecylsulfate-polyacrylamide gel electrophoresis (SDS-PAGE) result of the novel bacteriophage ΦCJ21.

FIG. 3 is an electrophoresis photograph showing a result of SDS-PAGE performed on the bacteriophage ΦCJ21, and main proteins having sizes of about 40 kDa, 51 kDa, 53 kDa, and 70 kDa were observed. In FIG. 3, M is a protein that becomes a standard for measuring a molecular weight.

Example 5

Gene Sequence Analysis of ΦCJ21

In order to confirm genetic characteristics of the purified bacteriophage ΦCJ21, DNA of the bacteriophage ΦCJ21 was analyzed using a FLX titanium sequencer (Roche), which is a gene analysis apparatus. Genes was assembled at Macrogen INC. using GS and de novo assembler software (Roche). Sequence analysis of an open reading frame was performed using GeneMArk.hmm, Glimmer v3.02, and FGENESB software. Identification of the open reading frame was performed using BLASTP and InterProScan program.

The genome sequence of the bacteriophage had various similarities with that of the existing reported bacteriophage, but it was confirmed that a bacteriophage of which all of the fractions were completely (100%) equal to those of the bacteriophage of the present invention did not exist. Therefore, it may be confirmed that the bacteriophage was a newly isolated bacteriophage.

Homology analysis data of nucleic acid sequence between bacteriophage ΦCJ21 and other bacteriophages is shown in table 1.

TABLE 1

| Query | | | | Subject | | Identities | |
|---|---|---|---|---|---|---|---|
| Name | Length | Start | End | Description | E-Value | Match/Total | Pct.(%) |
| contig00001_orf00003 | 543 | 70 | 537 | conserved hypothetical protein [*Clostridium botulinum* BKT015925] | 3E−05 | 42/161 | 26 |
| contig00001_orf00010 | 207 | 1 | 204 | hypothetical protein phi34O_gp33 [*Clostridium* phage phiCP34O] | 2E−12 | 32/68 | 47 |
| contig00001_orf00011 | 543 | 19 | 496 | hypothetical protein CbC4_4068 [*Clostridium botulinum* BKT015925] | 5E−17 | 63/180 | 35 |

TABLE 1-continued

| Query | | | | Subject | | Identities | |
|---|---|---|---|---|---|---|---|
| Name | Length | Start | End | Description | E-Value | Match/Total | Pct.(%) |
| contig00001_orf00013 | 588 | 7 | 570 | thymidine kinase [*Clostridium butyricum* E4 str. BoNT E BL5262] | 2E−55 | 109/190 | 57 |
| contig00001_orf00009 | 363 | 34 | 294 | putative phage related protein [*Selenomonas ruminantium* subsp. *lactilytica* TAM6421] | 6E−09 | 34/87 | 39 |
| contig00001_orf00017 | 528 | 247 | 360 | hypothetical protein [*Pelotomaculum thermopropionicum* Si] | 0.0003 | 17/38 | 44 |
| contig00001_orf00016 | 1974 | 133 | 1556 | primase [*Gordonia* phage GTE2] | 3E−36 | 137/494 | 27 |
| contig00001_orf00031 | 930 | 7 | 888 | hypothetical protein [*Gordonia* phage GTE2] | 5E−13 | 80/324 | 24 |
| contig00001_orf00030 | 2442 | 226 | 2388 | DNA polymerase 1 [*Gordonia* phage GTE2] | 2E−97 | 265/755 | 35 |
| contig00001_orf00024 | 762 | 358 | 756 | thymidylate synthase [*Clostridium acetobutylicum* DSM 1731] | 8E−16 | 45/134 | 33 |
| contig00001_orf00035 | 513 | 1 | 273 | hypothetical protein CbC4_7040 [*Clostridium botulinum* BKT015925] | 9E−18 | 48/91 | 52 |
| contig00001_orf00032 | 884 | 48 | 702 | gp089 [*Lactococcus* phage KSY1] | 2E−06 | 57/220 | 25 |
| contig00001_orf00036 | 1452 | 54 | 1437 | domain protein, SNF2 family [*Bryantella formatexigens* DSM 14469] | 4E−56 | 150/475 | 31 |
| contig00001_orf00026 | 163 | 18 | 180 | hypothetical protein AC5_1713 [*Clostridium perfringens* CPE str. F4969] | 6E−08 | 30/70 | 42 |
| contig00001_orf00038 | 441 | 31 | 384 | putative protein [*Aquifex aeolicus* VF5] | 1E−10 | 54/152 | 35 |
| contig00001_orf00044 | 1359 | 583 | 753 | hypothetical protein PCC7424_5514 [*Cyanothece* sp. PCC 7424] | 1E−05 | 31/57 | 54 |
| contig00001_orf00045 | 1248 | 7 | 1239 | endolysin [*Clostridium perfringens* E str. JGS1987] | 3E−158 | 295/415 | 71 |
| contig00001_orf00050 | 2913 | 2455 | 2904 | hypothetical protein AC3_2545 [*Clostridium perfringens* E str. JGS1987] | 6E−58 | 107/150 | 71 |
| contig00001_orf00052 | 1059 | 28 | 1047 | putative base plate assembly protein: putative PBSX prophage protein [*Bacillus subtilis* subsp. *subtilis* str. 168] | 4E−52 | 119/341 | 34 |
| contig00001_orf00051 | 588 | 28 | 573 | hypothetical protein HMPREF0830_00205 [*Eubacteriaceae bacterium* CM2] | 3E−15 | 55/184 | 29 |
| contig00001_orf00048 | 150 | 1 | 135 | hypothetical protein CLJ_B2512 [*Clostridium botulinum* Ba4 str. 657] | 9E−12 | 33/45 | 73 |
| contig00001_orf00047 | 213 | 1 | 207 | bacteriocin uviB homolog [*Clostridium perfringens* C str. JGS1495] | 3E−22 | 47/69 | 68 |
| contig00001_orf00049 | 594 | 1 | 585 | conserved hypothetical protein [*Clostridium perfringens* E str. JGS1987] | 1E−25 | 75/198 | 36 |
| contig00001_orf00056 | 714 | 19 | 429 | ZkdP [*Bacillus* sp. JS] | 9E−19 | 53/139 | 38 |
| contig00001_orf00055 | 987 | 1 | 960 | hypothetical protein 2016_scalfold57_00038 [unidentified phage] | 1E−41 | 110/328 | 33 |
| contig00001_orf00053 | 496 | 1 | 381 | hypothetical protein PlanB_05085 [*Paenibacillus, larvae*-subsp. *larvae* B-3650] | 3E−14 | 47/131 | 35 |
| contig00001_orf00057 | 2562 | 25 | 1239 | phage tail tape measure protein. TP901 family (*Herpetosiphon aurantacus* DSM765] | 1E−88 | 194/410 | 47 |
| contig00001_orf00059 | 420 | 88 | 417 | hypothetical protein BSSCB_30350 [*Bacillus subtilis* subsp. *subtilis* str: SC-8] | 3E−13 | 40/111 | 30 |
| contig00001_orf00063 | 435 | 1 | 339 | hypothetical protein putative PBSX [*Bacillus amyfolique factens* XH7] | 1E−07 | 37/116 | 31 |

TABLE 1-continued

| Query | | | | Subject | | Identities | |
|---|---|---|---|---|---|---|---|
| Name | Length | Start | End | Description | E-Value | Match/Total | Pct.(%) |
| contig00001_orf00064 | 534 | 43 | 522 | hypothetical protein B1NLASEDRAFT_3746: [*Bacillus* sp. 1NLA3E] | 1E-45 | 89/170 | 52 |
| contig00001_orf00065 | 563 | 13 | 336 | hypothetical protein B1NLA3EDRAFT_3747 [*Bacillus* sp. 1NLA3E] | 8E-13 | 45/108 | 41 |
| contig00001_orf00060 | 432 | 10 | 420 | hypothetical protein RUMOBE_01063 [*Ruminococcus obeum* ATCC 29174] | 6E-16 | 47/139 | 33 |
| contig00001_orf00069 | 1260 | 1 | 1089 | hypothetical protein RUMOBE_01052 [*Ruminococcus obeum* ATCC 29174] | 2E-02 | 153/300 | 39 |
| contig00001_orf00068 | 921 | 10 | 882 | conserved hypothetical protein [*Bacillus cereus* 03BB108] | 4E-86 | 185/201 | 58 |
| contig00001_orf00066 | 405 | 16 | 402 | hypothetical protein RUMOBE_01056 [*Ruminococcus obeum* ATCC 29174] | 5E-10 | 44/130 | 33 |
| contig00001_orf00070 | 885 | 19 | 879 | head morphogenesis protein SPP1 gp7 [*Bacillus* sp. 1NLA3E] | 7E-50 | 118/300 | 39 |
| contig00001_orf00081 | 1332 | 1 | 1329 | Phage tail sheath protein [*Desulfosporosinus youngiae* DSM-17734] | 1E-63 | 169/449 | 37 |
| contig00001_orf00072 | 398 | 1 | 372 | hypothetical protein 2016_scalfold57_00101 [unidentified phage] | 4E-11 | 59/135 | 43 |
| contig00001_orf00071 | 1467 | 46 | 1449 | hypothetical protein RUMOBE_01050 [*Ruminococcus obeum* ATCC 29174] | 5E-108 | 215/479 | 44 |
| contig00002_orf00002 | 637 | 259 | 678 | phage terminase, small subunit/PBSX family [*Clostridium bolulinum* [Ba4 str. 057] | 2E-25 | 66/164 | 40 |
| contig00004_orf00001 | 408 | 1 | 357 | CMP/dCMP deaminase zinc-binding protein [*Methanphalobium evestigatum* Z-7303] | 2E-23 | 56/131 | 42 |
| contig00003_orf00004 | 420 | 1 | 417 | gp317 [*Bacillus* phage G] | 5E-24 | 67/154 | 43 |

A partial genome sequence of bacteriophage ΦCJ21 prepared in the above is the same to SEQ ID No: 1. The genome sequence was determined by genetic analyzer.

Example 6

Stability Test of ΦCJ21 Depending on pH In order to confirm stability of the bacteriophage ΦCJ21 in a low pH environment, stability test was performed over a wide pH range (pH 4.0, 5.5, 6.4, 6.9, 7.4, 8.2, 9.0, and 9.8).

For test, various pH solutions (Sodium acetate buffer (pH 4.0, pH 5.5, and pH 6.4), Sodium phosphate buffer (pH 6.9 and pH 7.4), and Tris-HCl solution (pH 8.2, pH 9.0, and pH 9.8)) were prepared at a concentration of 0.2 M, respectively.

After 90 μl of each of the pH solutions was mixed with 10 μl of bacteriophage solution having a titer of $1.0 \times 10^9$ pfu/ml so that a concentration of each of pH solution became 1 M, each of the pH solutions was left at room temperature for 30 minutes, 1 hour, and 2 hours. Then, the reaction solution was diluted step by step, 100 of the diluted solution at each step was dropped and cultured at 30° C. for 18 hours by a soft agar overlay method, and the titer was measured through the presence or absence of lysis (FIG. 4).

Figure 4:
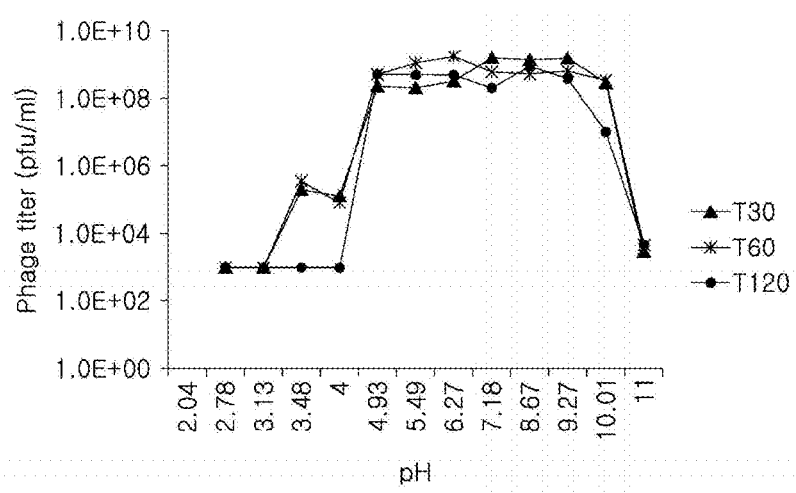
FIG. 4 is a graph showing a result of an acid resistance test of the novel bacteriophage ΦCJ21.

FIG. 4 shows a result of the acid resistance test of the bacteriophage ΦCJ21. As shown in FIG. 4, it may be confirmed that the bacteriophage ΦCJ21 did not lose its activity and was significantly stable in a pH range of 4.0 to 9.8 for up to 2 hours.

Example 7

Stability Test of ΦCJ21 Depending on Temperature

A test for confirming stability against heat generated during a formulating process of the bacteriophage in the case of using the bacteriophage as a feed additive formulation among formulations of the bacteriophage was performed.

In detail, 2000 of bacteriophage ΦCJ21 solution having a titer of $1.0 \times 10^8$ pfu/ml was left at 60° C. for 0, 10, 30, 60, and 120 minutes. Then, the solutions above were diluted step by step, 10 μl of each of the diluted solutions was dropped and cultured at 30° C. for 18 hours by a soft agar overlay method, and the titer was measured through the presence or absence of lysis (FIG. 5).

Figure 5:
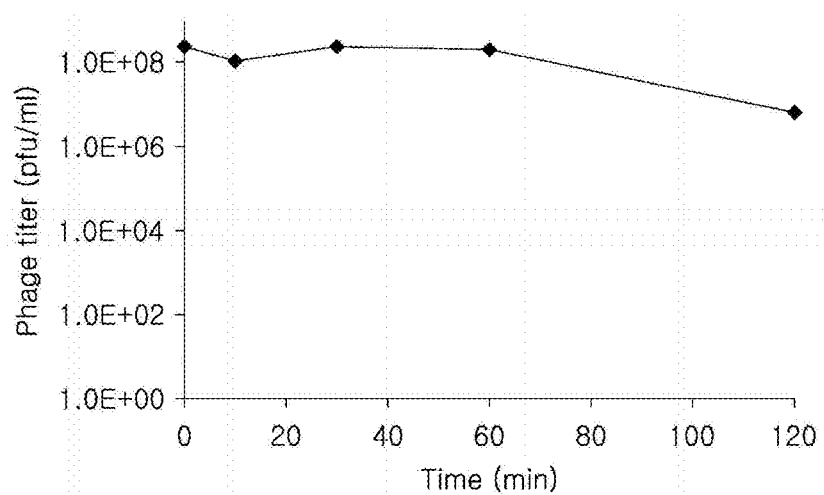
FIG. 5 is a graph showing a result of a heat resistance test of the novel bacteriophage ΦCJ21.

FIG. 5 shows a result of a heat resistance test of the bacteriophage ΦCJ21. As shown in FIG. 5, it may be appreciated that the activity was not significantly decreased until the bacteriophage ΦCJ21 was exposed at 60° C. for 2 hours.

Example 8

Stability Test of ΦCJ21 Against Drying

A test for confirming stability against drying conditions generated during a formulating process of the bacteriophage in the case of using the bacteriophage as a feed additive formulation among formulations of the bacteriophage was performed.

In detail, 100 μl of bacteriophage ΦCJ21 solution having a titer of $1.0 \times 10^8$ pfu/ml was dried at 60° C. for 120 minutes using a speed-vacuum (Speed-Vacuum Concentrator 5301, Eppendorf). The pellet obtained after drying was put and resuspended in a SM solution at an amount equal to that of an initial solution at 4° C. for one day.

Figure 6:
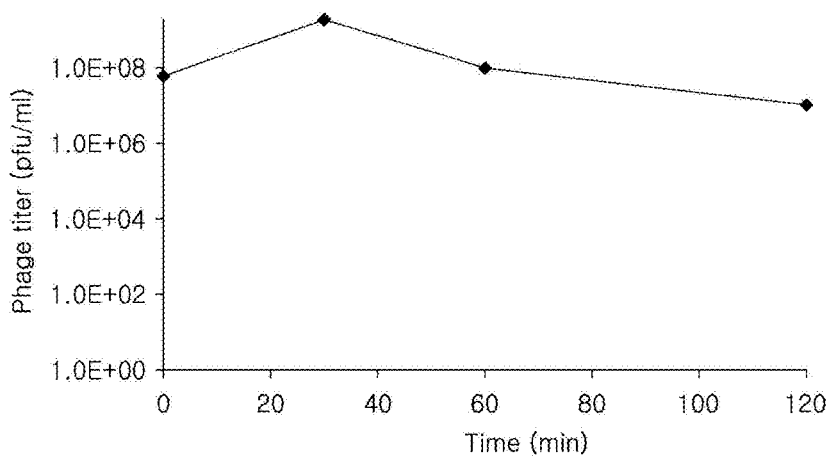
FIG. 6 is a graph showing a result of a drought resistance test of the novel bacteriophage ΦCJ21.

Then, the solutions above were diluted step by step, 10 μl of the diluted solution at each step was dropped and cultured at 30° C. for 18 hours by a soft agar overlay method, and the titer was measured through the presence or absence of lysis (FIG. 6).

FIG. 6 shows a result of a drought resistance test of the bacteriophage ΦCJ21. As shown in FIG. 6, it may be appreciated that the titer of the bacteriophage ΦCJ21 after drying was decreased to about 1/10 of the titer before drying.

Example 9

Infection Spectrum Test of ΦCJ21 with Respect to Wild-Type Strains of *Clostridium perfringens*

Whether or not the bacteriophage ΦCJ21 had a lytic activity was tested on 45 wild-type strains of *Clostridium perfringens* isolated by Animal and Plant Quarantine Agency and Kunkuk University other than *Clostridium perfringens* (BCCP 17-1) used in the experiment.

In detail, 10 μl of bacteriophage ΦCJ21 solution having a titer of $1.0\times10^{10}$ pfu/ml and mixed with 150 μl of a shake culture solution ($OD_{600}$=2) of each of the strains was dropped and cultured at 30° C. for 18 hours by a soft agar overlay method. Then, whether or not a plaque was formed was observed.

As a result of the experiment, among 45 wild-type strains of *Clostridium perfringens,* 44 strains were infected, such that an infection ratio was about 97.7% and a lysis ratio was about 97.7%. The results were shown in Tables 2 and 3.

TABLE 2

| Origin of CP | CP strain | Infectivity |
|---|---|---|
| Kunkuk University | HLYS-1 | + |
| Kunkuk University | HLYS-3 | +++ |
| | JSH-1 | +++ |
| | KCCM $40947^T$ | +++ |
| | KJW-2 | ++ |
| | OYS-2 | +++ |
| | KCCM 12098 | +++ |

TABLE 3

| Origin of CP | CP strain | Infectivity | CP strain | Infectivity |
|---|---|---|---|---|
| Animal and Plant Quarantine Agency | CP-KJW-1 | +++ | BCCP43-1 | +/− |
| Animal and Plant Quarantine Agency | CP-JSH-1 | +++ | BCCP44-3 | +/− |
| | CP-OYS-2 | +++ | BCCP47-2 | +++ |
| | CP-BC-1 | +++ | BCCP48-3 | +++ |
| | CP-BSW-4 | +++ | BCCP50-1-3 | + |
| | CP-HBM-2 | +++ | BCCP50-1-8 | ++ |
| | CP-HL | +++ | BCCP51-1-1 | +++ |
| | CP-KW-1 | +++ | BCCP51-1-5 | +++ |
| | CP-BS-1 | − | BCCP52-2-8 | +++ |
| | CP-HL-1 | +++ | BCCP53-2-3 | +++ |
| | CP-LJN-1 | +++ | BCCP54-3-8 | +++ |
| | BCCP17-1 | +++ | BCCP55-3-1 | +++ |
| | BCCP23-4 | +++ | SBCCP429-2 | +++ |
| | BCCP37-2 | +++(T) | SBCCP321 | +++ |
| | BCCP38-1 | +++ | SBCCP343 | + |
| | BCCP39-1 | +++ | SBCCP361 | +++ |
| | BCCP40-1 | + | ELCCP Suksan Kim | +++ |
| | BCCP41-3 | +++ | ELCCP6-1 intestines | +++ |
| | BCCP42-2 | +++ | appendix | ++ |

The invention claimed is:

1. A method of preventing or treating an infectious disease caused by *Clostridium perfringens*, comprising administering, to an animal excluding human, a bacteriophage ΦCJ21 (KCCM11363P) having a bactericidal activity against *Clostridium perfringens* or a composition comprising the bacteriophage ΦCJ21 (KCCM11363P).

2. The method of claim 1, wherein the infectious disease is necrotic enteritis.

3. A method of preparing an animal feed composition, the method comprising:
   providing a bacteriophage ΦCJ21 (KCCM11363P); and
   mixing the bacteria with an animal feed base to provide the animal feed composition.

4. The method of claim 3, wherein the bacteriophage is in an amount of 0.05 to 10 by weight based on 100 parts by weight of the feed composition.

5. A method of feeding, the method comprising:
preparing the animal feed composition according to the method of claim 3; and
feeding the animal feed composition as a feed to an animal.

6. A method of preparing a drinking water composition, the method comprising:
providing a bacteriophage ΦCJ21 (KCCM11363P); and
mixing the bacteriophage with drinking water to provide the drinking water composition.

7. The method of claim 6, wherein the bacteriophage is in an amount of 0.0001 to 0.01 by weight based on 100 parts by weight of the drinking water.

8. A method of feeding, the method comprising:
preparing the drinking water composition according to the method of claim 6; and
feeding the drinking water composition as a feed to an animal.

\* \* \* \* \*

UNITED STATES PATENT AND TRADEMARK OFFICE
CERTIFICATE OF CORRECTION

| | |
|---|---|
| PATENT NO. | : 9,745,555 B2 |
| APPLICATION NO. | : 14/767269 |
| DATED | : August 29, 2017 |
| INVENTOR(S) | : Bo Kyung Son |

It is certified that error appears in the above-identified patent and that said Letters Patent is hereby corrected as shown below:

In the Specification

In Column 2 at Line 40 (approx.), change "Korea" to --Korean--.

In Column 7 at Line 27, change "smae" to --same--.

In Column 9 at Line 49, change "Samwhaw" to --Samhwa--.

In Column 9 at Line 50, change "Chungchong" to --Chungcheong--.

In Column 10 at Line 21, change "120" to --12 ml--.

In Column 10 at Line 22, change "500" to --500 µl--.

In Column 11 at Line 3, change "bacteriocidal" to --bactericidal--.

In Columns 11-12 at Line 63 (approx.), change "496" to --486--.

In Columns 13-14 (TABLE 1-continued) at Line 12 (approx.), change "Si]" to --SI]--.

In Columns 13-14 (TABLE 1-continued) at Line 30 (approx.), change "163" to --183--.

In Columns 13-14 (TABLE 1-continued) at Line 30 (approx.), change "18" to --16--.

In Columns 13-14 (TABLE 1-continued) at Line 38 (approx.), change "contig00001_orf00045" to --contig00001_orf00046--.

In Columns 13-14 (TABLE 1-continued) at Line 65 (approx.), change "496" to --408--.

In Columns 13-14 (TABLE 1-continued) at Line 71 (approx.), change "aurantacus" to --aurantiacus--.

Signed and Sealed this
Twenty-second Day of May, 2018

Andrei Iancu
*Director of the United States Patent and Trademark Office*

CERTIFICATE OF CORRECTION (continued)
U.S. Pat. No. 9,745,555 B2

In Columns 15-16 (TABLE 1-continued) at Line 7 (approx.), change "563" to --363--.

In Columns 15-16 (TABLE 1-continued) at Line 10 (approx.), change "6E-16" to --8E-16--.

In Columns 15-16 (TABLE 1-continued) at Line 14 (approx.), change "2E-02" to --2E-62--.

In Columns 15-16 (TABLE 1-continued) at Line 14 (approx.), change "153/300" to --153/390--.

In Columns 15-16 (TABLE 1-continued) at Line 18 (approx.), change "185/201" to --165/291--.

In Columns 15-16 (TABLE 1-continued) at Line 18 (approx.), change "58" to --56--.

In Columns 15-16 (TABLE 1-continued) at Line 28 (approx.), change "contig00001_orf00081" to --contig00001_orf00061--.

In Columns 15-16 (TABLE 1-continued) at Line 31 (approx.), change "398" to --396--.

In Columns 15-16 (TABLE 1-continued) at Line 38 (approx.), change "637" to --837--.

In Columns 15-16 (TABLE 1-continued) at Line 38 (approx.), change "2E-25" to --2E-26--.

In Columns 15-16 (TABLE 1-continued) at Line 40 (approx.), change "bolulinum" to --botulinum--.

In Columns 15-16 (TABLE 1-continued) at Line 41 (approx.), change "str. 057]" to --str. 657]--.

In Columns 15-16 (TABLE 1-continued) at Line 44 (approx.), change "[Methanphalobium" to --[Methanohalobium--.

In Column 15 at Line 62 (approx.), change "100" to --10 μl--.

In Column 16 at Line 56 (approx.), change "2000" to --200 μl--.

In Column 17 at Line 32, change "kunkuk" to --Konkuk--.

In Column 18 at Line 8 (approx.), change "kunkuk" to --Konkuk--.

In Column 18 at Line 9 (approx.), change "kunkuk" to --Konkuk--.

SEQUENCE LISTING

```
<160> NUMBER OF SEQ ID NOS: 1

<210> SEQ ID NO 1
<211> LENGTH: 47438
<212> TYPE: DNA
<213> ORGANISM: Artificial Sequence
<220> FEATURE:
<223> OTHER INFORMATION: a novel Clostridium perfringens specific
      bacteriophage KCCM11363P

<400> SEQUENCE: 1
ttttaaagag actgcaatag gttttctaaa aataagggag ggattaaccc tcctttttat     60 aatttttga gttctggaaa aatccttaat tagttcaagt ttcgtgaagt tctcttgatc    120
ttctccattc tcttcttaac ttggatagct tcttcttcgc aatgagcatg gccatccagg    180
aattggtgcc atcttctttc aagttctctg tattcagatt gaagttctat aacctcaagt    240
gaatggttgt ccatagtatc acctccttaa cactattata agtgatactg tcatattctg    300
tcaaataaaa aagagaggta atatatacct cccacattat cttattgagt atacacagat    360
atattcttct tcaagagttt ggttaataag tgattgagca tatttgtata gatctttagg    420
```

```
ttgtgtatct cttatatctt gtattacttc ttcatgttct cttcttaata atttatatcc    480
aaagcataat gggttctcct caagttcaaa taatatttcc cagttagtca ttttattata    540
attcatattt aacatctcct tcagtttgtt tatgctttaa ttataagaga gagtccagag    600
agtgtcaata gaaatcccga agaaaagag agaatgttat tctccccatc ttaatatttt    660
tattgttgct ccatcaactc ccttgccatc cacatcatgg acatacttat caagtctcat    720
tgttgagtcc tgtataactc ttttgtcttc tctatcaaaa accttaatga catcagggtt    780 accctgtca atgatgtaag caatctcttg agttccatct gcatatgtta cttgaagtaa    840
tgagtgtaga ggtataaagt ctggagctgc ccagtcacca accttaagat ctcctcctat    900
actattcttg gtctcatatc ctgccacatc tgtaggttca tctgatgaat aataagtaac    960
ttcaactttg aactccattc ctttaaatga atttatcatc tcaattagat tttgtttatc   1020
agttctcagt ttatcattct gatactttaa tccttctaca ttatccatca gtatttcagt   1080
ctgctcagtt aattgtttat ttgactcaat gtattcttgg acagcattcc cccaatgatt   1140
gtttaggctc tgtatggtta acagtagccc tcctatcaca attattgtta ataatgacat   1200 aattcttta atcattctct tttaactcct ttatttttaa tttgaatttc tcaattccag   1260
atttatattt acccacagta ttaaaagtat cagttagtat tgcataggtt tcctcatcag   1320
aattaaatct gaagcttcct ctcttgatat cacctagctt attaaaggtc ttaccctcct   1380
tgtccagata tcctttatag tccatatagc acagacaagc agtaataaat tcctgtttag   1440
ttctgaagtg atgagatata cccataccct ctacccattt acttaataca aataggctct   1500
cattatcctt tggctttatc aattcaatcc atacaaactc attagcttgc tttagattag   1560 taaactttt agccttgaac ttcttactac tctggatctt atccttatag tcatggaata   1620
cttcaggcca aaattcctgt aaatacatat ataagagaa ctcatctacc ttagctttag   1680
gatctttaaa gttaattaat gggtatccag acactgctct tatctggttc tttagcatat   1740
tattctcatt ttttagttga gaaacaatga aagagagatg agtaacagct ctggtaagct   1800
catgctcatt taaagatcta ccttctctat tctggattag cttccttaat tctccccagt   1860
tatctatcat ttatagcacc tcctatgctt acattataca tatataagat aaatatgtca   1920
aagtccacat aggcatatca gtatcatttt ttctgatatg ggtagcatat cagcatagtt   1980
acacctgata tcacatatag agtttacaat ttttgtaatc aaatttgttg gtatcactag   2040
cgtagaggga tatcagaaat accccatatt attacaatat atactatata taaataatta   2100
tatattatta tatatagtat atagccaagg gctatatata actatgtttt attgattaca   2160
taattggcag gctattgcct tgccttcgtt tacactacgg caggcatatc catgcaggac   2220
ttctcttccg agcttttgcc ctatatagaa aaacccagac ggtcagcgat cgagctcttg   2280
attttgtttg gttggaaaga aagagagagt taggggaaa gagagtaaga gagaacagta   2340
gttgagagag agttctcccg aacgttgaca gttgtactta cttctcttat aatgacagta   2400
aaggagggat aaccattatg aaagttatat tatctaatga aaaagaaatt atcattgaaa   2460
acaaggactt cttcataata atggaagagg acagatttat tctatctaga gcaatagata   2520
agaattgcgg agaattagta tctcaagtac ctaagtactg tattcttata tatgaggata   2580
aatccatacc aagatactta tataaggata atactcattt atatgaggtt attggcaata   2640
gagctatcat aagatacagt atataagagc ccacaatcaa ttctaaggcc ttttagatat   2700
gtggtaatgt gattttactt ataatgtggt agagacacct tacaggagct gctagaggcc   2760
tttaaaggag gtatatcatg tatttatgta atggtaaaat agtcaagaat aaaaatgact   2820
```

```
taaaagataa gtttggtggt aaatcagtag tattcatcga tggggatgta gccacagtaa    2880
tggactttag tgacagaaag ccaaagataa caaaatatct tattagggag gtatcacatg    2940
ataaacacat cattattgaa gagactggaa gggatagagg aaaagcataa gcaaaatact    3000
gatgagataa gaaagaacct aaactatgcc agatatttga ttgagaaaca gtattgtcat    3060
ttaacaaagg agcagaagat aaaattggga cagttcttag gattgactga gaagaagtta    3120
aaagaaatac aagagataaa taatcagtta ataaatttga gagtgggact aagttatgaa    3180
gtcgtatgta ataaccagaa aaaatagtgg ggtatcttta gcagatacag acatgggaca    3240
agtattagct aagatactat gtaagcatgg gggaacactt accattgagg aaattgaacc    3300
agaacatatt ggtcaaactt tttctattgt agaaggtaaa agaatatggt ataatagaaa    3360
aggaggtgat aatattgggg agaagaagtg ctatgttaat tctcaagtat gactgcgaag    3420
aaactccaga aagaattgaa ttacgaaaga agtggttaca ggtttgtctt cattcaataa    3480
tatattatag atatgacaac aatatctgga cagaccaaca atgggatgag actgccagag    3540
aggtagttaa acttaagaat gagaatccag gcttagtaaa cagtatgcca tttaggaatg    3600
accttaaaat ctttgatgga tccactggct ttaatctttc atgtatgcaa gatattaaga    3660
tgctaaggtg ggctcaaaat ttactcgact ttcatgttaa acgaggactt gatggaaaga    3720
gtaagaaaaa aagaaaagg aggagaaagg aatgaaccta cttgagcact atataaaaaa    3780
ggtacacagt gtaagagagt accatgaatt cgataatgaa ccttgggcta aggtaaaca    3840 atatgtagaa gtagaccttg attatctttg ttactctaac ataccacaaa gaactaaatt    3900
agtatttact gttgatgagt gggagaaaat aaaatataga ggctactaca tgggataggg    3960
ggaatagtta tgataagaga aatgggcatg agaatgctaa taccagaaat acatgatata    4020
aaagataggg atatacaaaa ttttgtaaga aaggccctaa atgagctagt tgatgaaaag    4080
ttctttataa tacctgcaag tagtactggg aaatatcatc caacttatag tgcaggggta    4140
ggaggtttgc taagacatac taaagctgct tgttatatag gtaaagcatt atgcgaagct    4200
gagatgatat gtcaagaaga taaggatctg atacaggctg ctctgatatt acatgatatt    4260
aataaacctg ctaaggagca tccatatatg gttagagaga cactatcccc attaaaggaa    4320
gagtttccat caacctatga aaaggtaata gaactaattg agtctcatca tggtcaatgg    4380
ggagagtacc caattaatac ttatcaaaag aggatagtac acttagctga ttatatcagt    4440
tcacaaaaag gattaatatt ctcatatgac caaggaactg attattctga cttgttatgg    4500
gaggagaagt aaatggtgct agggtaata accctagtat caatattttt actaggagtg    4560
tttataggtt ttgaggtgaa gaaatggagc taggttttgc aatattagct atagtagtat    4620 caatatttt agaaactaaa tatataaagg agtagattat tatgtcaaga gcaagagctg    4680
caagaagaag agctgaaagg gagaacaaaa atcttaatgt tcttaaagct gtggacatca    4740
tgttagcctt atcatgctat acattaaaga aggaaggtta tggtaagact agaatgacta    4800
ggtttgtgga agagatgagt aaacacacag aggaaattga aaagggaaca cttaactatg    4860
aaaccataat gggagagatt aaggatttag taccaccagg tatatttgat ttagaggagg    4920
agtcaaagga gtgataatct tggaataatt attatgggca tttagaatat taggcatact    4980
tgtaatagta tggtgtatat tggaggcgat cagttgtgag caataaatta tattttaggt    5040
atagtgctat gaactctgga aagactactc agttaatcca ggtagcacat aactatgaag    5100
aaaggggaat gaagccctta gtagttaagc caggaattga cactaaaggt ggaccatgta    5160
```

```
taatcagtag aatagggta gcaagaaagg tggatgttct tctacctcct agggttaaat    5220
tatcaaaaat actttctgac tttgaggcta attactgggc agtagatgtt atattaattg    5280
atgaggtaca attcttatcc agagaacagg ttgatgatct gttaaattta tcattacatt    5340
atcctatcat atgttatgga ttgagaactg attttaaaag agaaggattt gaaggaagta    5400
cccgattatt acaagtggcc cataacattg aagaattgaa gaacatttgt caatgcggta    5460
aaaaagccac attctcaata ttgaaatatc aaggtaaata tactgaccag ggtaaccaga    5520
tacaaattga taaccagcca gaaagtgttg aatatgaagc cgtttgtaat gaatgttata    5580
ataaattaat tttttctaaa taactcgttg acaggctata taggatatga tattatagta    5640
ttgtaatcaa attacaaaca ccaaccaaaa ctttataatt agttaatttc aaactatact    5700
aaatttgtta tttaaaaatt aaaaatatgg aggaatgatt attatggcaa aaggaaaagc    5760
aaaatggtta gaggaagcaa ataataagga gttaattgta atagtacaat ctgctttaaa    5820
ttctggagat gagaaagaag ttaaaaaggc tttaaaagct attgtggaat tagatgaaag    5880
aactcctgac acagatggac aaataactgt agaggaagca ttagaatcat tagaaatggc    5940
tgtaggaact gtaaaggctg cataccaagc agaaatagat gctgtggaag atgaagatgc    6000
agtagatgct gacttcgaag aagttgatga agacgaagca gaagaagatg aaaatgattt    6060
agaatcatta tctaaaaaag aattagctgc tatggctaaa gacttaggta tcaaaggagc    6120
taagaaaaaa gataaagatg agttaatcgc tttaatcaaa gaagctcaag gtgaagaaga    6180
agacgaagag gaagaagaag aggatgaaac tcctgactac tctgaaatga ctaagaaaga    6240
cttaattgct cttgctaaag aaagaggaat aaaagttaat aagaaaatga accagctga    6300 gataattgaa ttattagaag ctgatgatga agaataattc tcatcaaatt ataaggggag    6360
caaacttgct cctcaaattt tttacttatt ttagaaacag atgttagagg gggatgtata    6420
aatggcaaga ggtggaaatt caacttatac taaagcagta tattgttaca acaataatag    6480
ggagtataga tccttcagat atgcagctaa acaattagga gtatcggctg ttagtataat    6540
gagagtagtt aacgggacta aaccacatat agggggatta gtattcgctg agatagagga    6600
aggcactaga aaattaaagc caagaggaga agtagttcca tacttgaaag aattaggttg    6660
ggataatata gacttataat aggggtata atatatggac ataaagttct tgaaggatat    6720
attctctaaa caatgtgaaa atggagatta cattatccta gcagctagaa aaggtaaaga    6780
atggaaagat ttaccaatta aatataataa gaataacatt gacaaaaaac taaaggactt    6840
tgaacaacag tataagggtt atgatttata ttggagccca atgccttata gtaatcctca    6900
aagaaggata gttaacttca tagagactaa atacttaata caagatatag atgagcatac    6960
tgacccattg gggattaaac ctaaaccaag ttatctgtgg gaaagttctc ctggaaaata    7020
tcaggggcta tgggaaatgg ataggtatat agaggctaat caatatgacg aaataaatcc    7080
agcattagct aaacatatag gctgtgactc ctgctttgat gttactcatg tatatagaat    7140
accaggaact attaactaca aatacaagaa taaaccaaaa gtaaaaagac ctatacacac    7200
taaggagata tataagccta aggtgatcgc taaggctgtt aaggctgtaa gtaaatctaa    7260
tgatagtgtt aaggtcaata taggaggatc tgaggcctca caatctgaaa gaaagatata    7320
tgctaaatat aatataccaa agaaggttag agacttactg gctttagatg atattacttc    7380
tttagataga agttctacta tatggtatat tgagaataag ttacatgaaa taggactaga    7440
gcctaatgag attatattat tagttaaggg ctcagctttt aataaatata agggaagaaa    7500
agatgaagaa acaagattaa gaaagaatt ggataaaatc ataggaggag aaatagaggc    7560
```

```
tgatattgaa aaggctgaaa gtactaaact gagaatagat agttatcagg atgttatggg    7620
taataatgga gccttccagg gttggttagt acaaggtttc tggggtagaa gatctcatgg    7680
aattgtggct ggacaaccaa aggtatttaa atccacattt acacaggact tagctatatc    7740
agttgctagt ggaagaccat tcctaggtca atatcctgtt ctagaaccag gcccagtaat    7800
tgtagttcaa aatgagaatg ctgactggat tatgagggat agaactgaaa agataattag    7860
ccacagagga gtagttggta atgtggatat aaaaggtaag agaagactta aagttaggtt    7920
tgctccagat cttcctatca cttttattaa tcaacaggga tttatgttag atgaagaatc    7980
ccatagaaaa cagatagaag aattaattga tgagataaaa cctgtactag taatattcga    8040
cccattatat cttatgttta gtggagatct taataatgca gctgatctta atcctgtact    8100
acaatggtgt cttaaactta agaatgagaa gcatacagga gttatgttaa tacaccacta    8160
taataaaggt ggaaatgcca ctcaaaccag aggtggtcaa aagatggctg gttcattcat    8220
attacatggt tgggtagaat cagcactata tttaaaaaga cctgatgact agaaggtga    8280 cgatgaggag atcgaggtag atatagataa ccttgataaa caaagccatt taccaagtaa    8340
aatcattatg gatagagagt tccgtcttgc aggacaattc cctcaaattg aattaaattt    8400
atcaatggga gaatttggag atccctatta tcatgtagaa gtagcaatac ccggaaaaga    8460
agtaattgtg aaacctgagg acaaagccaa agttatagag gctgtaaaat caggagctca    8520
taccaaggag gagatagtat caatatcagg attaaattca cagaaggtta atctagttct    8580
agatacttta aaagatacta ttgtatattc tccggataaa ggttataata taagtaagaa    8640
actaaatatt gggaggaaaa aggcatgata ataaagtgta agaggccagc aggtcataat    8700
catataaagg cctttgtagt agtaattatt gctaggggta agaagaataa aatcacttat    8760
cattcaggat tgaaatattt ctatacctat aaatcagcta aattatttat agacaaagtt    8820
atggaagaat gtccctgggc tgaatttttat tgggtggatg tccatgaagc tcataagatc    8880
cctgaaggcg aagaaatacc caaaagaag atgtggtgtc atattgtca aactattcaa    8940 gaatttaaga gaagccaagg aggttacaag aattgcccta tctgtggtat aagtgaccaa    9000 gactttatg taaaatgtat gaatataaag tatagggagg ctaaggctaa tgcgaagaag    9060
aaacttgaag gaagtagtac taattctagg gatatcattg tcaatgggga taatgctaac    9120 tcaggggca aaactaatag aaagtcatca ccaaagaaaa agtcaagaaa agttagtaga    9180
aaagcttcat aatgctttag actataatgt tattgagact tctccatctg gactagatgg    9240
ggaggatctt accatcaaac taaatcttaa tagtcctaag gaccttaccc ctaacaactt    9300
atctaagtta gctaatgagg ttatggtcaa taacttagga gctcagaatt atactatact    9360
tgtttatgat agtaatagac cagaaaatct tctggctgtt atagatatac ctaaaaattc    9420
taaaataacc tttgacataa taaattaatt atggtaatat aaaaatgtag aaggaggaga    9480
atttaatggt caataaaaag tattacatct tgaaagacct taatgatgac aaaccccaac    9540
tatggaaggg aagtttaacc actgctacta agatagcagg agcattagga gttagtgtga    9600
taaaactaaa taggtattta gtaagaaagg gatttgccag aagtacaat gagcatacac    9660 ttgaaataat agacccaatc cttgctaaag aacttggtta ttatgtaact ccaagtaagt    9720
cccttataaa tccttttatt gaatataatg ataaaggagt acaatatata ctaaacttaa    9780
tagtagaaga tctaaagaat ggaggagagc tttaatgatt atcattttag gaatggataa    9840
ctcaggtaag accacaacag ctaagaacct aactaaacac agaggaggag aatatatcca    9900
```

```
atcaatggga cctggttctt atgaagaaca agagaatgg gtattaactc aaattgtgag    9960
aaaaggtgaa agggaagcta tacatgatag atttacttgc tttgaagaaa tggtgtatgg   10020
acctatcatc agagataata gtaatttcaa ccttgacagt aaggagctaa agatcttaaa   10080
acatctatgt aagccaacta ttgtatatgc tagaccacct agggaagtga tcttcaattt   10140
tggtgataga gaacagatgc caggagtaat tgaaagagct gaacatctac tagctagata   10200
tgatgaactg atatggaaat tattctgtga tggatggaat gtactggtat atgattatac   10260
tacttccaat gtggagaagc tatcccaatt aatagatgac tcaagtgcta agaagctat    10320
aaaccaattt ataaatatat caagataaga ggagagattg ttatgaatat aaaccatgca   10380
gtagaagaaa aatagaagg agatagatta caagctatct ttaatagaca aaaggaattg    10440
atggagaaat atcatcatat agaggctaga tcaggattat gccaaactga agactgtcca   10500
gttaacttaa atgataaaag gggtcaagct agacttaaag attttgcttg gagaatgact   10560
gaagaagtag gagaagcatt agatgcttat aaccatgaag accattacca agaagaattg   10620
attgatggat tacacttctt aactgaattt acaatcctag ctggtaagga ttataatact   10680
atagatgata atgctatact agttgatagc ctagagaact tatatcataa ggctactaca   10740
tcaccagaat ttcctgaaat gttagtagaa gaagctgtaa ctgacctggt aagagaaatg   10800
ggtatgtgct gtaattgcct taagaataaa ccttggaaac aaacttcaat gctaacagat   10860
gtaaatgctt ttaccaaag actatttaat gtatgggtat gttatattaa attattagct   10920
gtatctggct tagaggtaga tgacatagta aatatatacc ttaagaaatc acaggtaaat   10980
aaattccgcc aaagatctaa ttactaaaat aaatacttag gagaaggtaa tatgctaata   11040
agagactata atgattttga tgacttattc ttaaatctta atagggaaat gattaccaat   11100
ccagaagaaa ctatgatgta tactcagaat atacagggct ttcaggagga cttagttctc   11160
tcctgtaagt cccataaatg tactttaaat ctaggggact ttggatataa agaaggtaag   11220
tggggacacc tattaagatc atacattgat tatccacaat taattgaatt tagagaaaag   11280
cttaccaaga taagtggtat gagctatact tattatttca acaggaaaaa agctactaat   11340
ggttcttgct tgatagctgc agtagtaact agaccaaaaa gaaaaggacc ttggaaacac   11400
ttaaaaatta tgtatagagt atgtgaatta caaaagaaat tcgcagctga cctagtatta   11460
ataaacaggt tcattgaaga actacctcaa gaagtatgtg agatagataa tattacttt    11520
catatgtctc aagcttattt gtcaggaatg tttataaatg gatacttcaa ttatttttaag  11580
gtaccaagaa agagtattgc taatagcaaa catccttggc ataaatcctt gaatagtaac   11640
tataacaggt tctttaaatc agaggaccag atacactctt acaaagctct ccagaagatg   11700
cagttattac attttggtct ggagaaattt ccaaagatag atatcaataa attatctatt   11760
gacaagtact ttaataagta gtataattaa cttaacaaaa ttaaataaat ggaggaatta   11820
aactatgaga atttatatta atgctcaaga agcatttgaa gaagtaaaaa gagatttatg   11880
tgaaatgggg attgaggtaa gacccaaaac tatgcaagat aaagttatag aaggtaatcc   11940
agattatttc acaaaggagt tacaaaacta tagttacaca attctagaaa gtaaacctga   12000
agaagttcca ggtgtatctc aaccttgggc agatgctgaa tttagagaaa ggatctacga   12060
tccacaaggt gtcatcaatc aatactctct tgaagaaaga gaagaattat ttggtataca   12120
tccacatcat actaggggg ctttcataaa tcccggtaaa gcttatcaat taagacctga    12180
ggtatggaat gaatatctaa gagatggaaa atttggatat tcttcaatg aaagaatttg    12240
gcaatacaga caaattgagg atatcatcaa tagaattaaa gaagatccag gctcaagaca   12300
```

```
attatggtta tctctgtgga atccagctat tgatccattc aatataggag gagtaactag   12360
agtaccatgt tcattaggat ataacttcca agtaagggaa ggtaaattaa atattcatta   12420
tgttatgaga agctctgact ttgctactca ctttgctaat gatgtttatc ttgctatgaa   12480
actattacat tgggtagctg aacaaactgg ctatgaacca ggaagtttct ctcatacaat   12540
tttctctctt catgtttaca acaaagatat taagggggta ttctaataaa tgagttacat   12600 gagaaagaa agatataagc attctgatct taataataaa gttaacaaga aagaaaccct   12660
aaagcaattt attaggaata ctgaaaagga atttgattta gaaccagcta accttgggga   12720
tatgactaga aatgaactta ataactatat aaattatatg gatgaactgt ggagtaagta   12780
atatgtataa ttatagtgat gataacagac ctaagaataa taacaatggc tgtcttggtt   12840
gtttaattat aatcttagca gctataggat tatgggtaat aattttgat attgccaata   12900 taatatatca tatgatattc taatttaaag ggggctatcc taatgaaaaa tataatttgt   12960
cctatgtgta aaaactcagt aacattaaaa agaaaatatg gagctatgtt ttggatcatg   13020
attttcttaa ctggaggcct atgggtagta accatacct tcaaaaaaca taaggtctgt   13080
ccagtatgta attcaatcat aaaataaaga taagggcctt taggggtcct ttctatttag   13140
gaggtaatat tttaaatgag atgtaacaac tgtaacctat atacccactc agctccctca   13200
tgtatagaag gaacttgtgt aggaaagaaa aagaagccaa gaataatggt cataaatagt   13260
ttagctaatg atagggatga ggccaataga atagctactc ctgataaatc attacttgat   13320
aaaatggaag gtctagactt ttattatacc aatgctatta agtgtagaac tcctaagggt   13380
actaaaatca aagtatcaga gattaagaaa tgccaagaac atttacttaa ggaaattgaa   13440
aagtataaac ctgagtatgt tatgatctta ggatctcaag cactaaagat gctaagtaat   13500
gaaggtataa cctcaatatg tggagtacct aaaaaacatg agaaatatgg ctttaagttt   13560
attgccagct attcaccagg tgtagttgca tatgacccaa ctaaagcaca atttgtagat   13620 caggcctta ataactttaa agccatggta aaaggtaaag agcatgaatt accagagctt   13680
aacataaaac ttattaccag tatgaaagag ttaaaccagg ctttcaaata tttaagagag   13740
gaaggttata atagagtatc atatgatata gaaactagag gcttagatag gtttaataat   13800
gacattactc tatttggttt tggtaatact caagtacaat atatactgcc tttagaagtc   13860
aaatatagcc cattaagggg taagcccata gcacaaagaa gattagctaa atccttgatt   13920
aaaagactta attcggagat gaaggaaaga atagcccaga atggtaagtt tgatgataat   13980
ttcttaaagg agaaatatgg tattaagcca atcataacct ttgatacttt actagcctca   14040
cattgtttag atgagaatac tcctaatggt cttaaggaga atgctttatt acattgtaat   14100
gctaaagact gggatataaa taagaaatta aagaccggaa atgtggagac taatcagac   14160 tttgaggatt atgttaggta tctggggtat gatatatact atacatttgc tctatataaa   14220
atatttaata aaagacttaa aagggatgag agcttatata aactattcca ccacttatac   14280
atcccagcta gtaaagctta tgaggatgtt cagttcaagg gtatatatgt aaatcaggag   14340
aaattcaaag aggttgaaaa atacttaaga tctgaactag ataagattga gactggactt   14400
aagaagtata ctaatggcca ggatattaac tggagctcac ctaaacaggt tggggaattt   14460
ttatatgata cccttggtct tcctgtgatt gaggttactg actctggagc accagctact   14520
ggagaaagtg tattattaag actaagagat aaacatccag cagtgaaact actattacag   14580 catagggag ttcatataca aatttctcac tttatagatg gttggctaaa taggatgcac   14640
```

```
aatcatagat tatatccaaa ctttaaactt catggaactg taacaggaag aacctcaagt    14700
aataatccta atctacagca agttcctaga gataagaaaa tcaggagttt attaggacca    14760
tctcctggaa gagtattcat tgaagccgat ctatcccagg ccgaacttag aatagctgct    14820
atgatggccg atgaggataa tatgaaattt atttaccaga ctggtggaga tatacatgac    14880
tccacatata atattatatc tggggaagat atcaatgatg agaaagatcc agcagttaag    14940
aaggagaaaa ggaaaaaggc taaggctgta aactttggtt tcttatatgg tatgcaatgg    15000
aaaaaattca aggattatgg aagagacaac tatggtctta aattaacaga tgaggaagcc    15060
aaaacatata gaaggaactt ctttaataaa tatcctaaac tattaacatg gcatgataaa    15120
caaagaaaga ttgttaaagc caatggtgaa gtaagatctc caataggaag aattagaaga    15180
ttaccagata tatattcatc tgatagatct aaagctgctg aagccgaaag acaatgtatt    15240
aactcaccag ttcaaggttt tggttcagat atcactttat taggcctatg tgagattaca    15300
ggctatgcta aatatgttaa tcctgaatat gtattagata agtctaagtt tgatgtatta    15360
ggctcagtac atgactcaat attatttgaa gtagataaag actatgtgga agaattagct    15420
tggaaagtaa aatcaatagt tgaaaataat aaagtattaa agaaagtatt taaatttacc    15480
ccaacagtcc caataatcat ggatatatca gttggttatt cttggggagg atgtgttgaa    15540 ctggattta aaggtgattg gaaaagccag ataagaaaag tgttgacaga tgaataatta    15600
tctgataata taaatattgt aatgaaaagg aggtataagg atgttaaaaa taagtaattc    15660
cagaattaac aaattcttgt cttgtcctta tgcccattat gttaaatact atgaaggtct    15720
ggtacctaaa agaagtggag ctgccttaca aaggggctct gctatccacc aggctataga    15780
agactaccat aatgggaaga gttggaaaaa atctgttgat aaattttcca aagagtttta    15840 caaaatataca tttaaagaag agatccttga atttggagat attccaaaaa tggtttattc    15900
tttatgtgat aactatttcc actattatga tgaaaaagaa gataatgtaa cctatgtgga    15960
aaatgaacat cacttcgaat taaaactatg taagggtgta actctagaag gctatattga    16020
tagtgtctta gatgtggatg aaagatatg ggctaaggaa actaaaacct ataaaaagat    16080
gcctgataga aatttcctga tcttcaatag acaatctgct atatatacct gggctcttct    16140
acatgaatac ccaaaagtaa gtggtactat atgggatata atattagctc agcaaccagg    16200
tagaccagaa ttaactcaaa aaggggtatt atctcaaaag aggattaaat ccacacctt    16260 agagttagaa agaggaataa gagaattagg attagatcct aaagattatg agtcttatat    16320
taattctgct agatgggaag acttctttgt aagacaccca ataatattat caaagagtat    16380
acttaacagt gtaatggatg atactattga gatagctaaa cttattagag atgagggtca    16440
caaaagaaag gaaagaacc ttggaaaagg ttgctctttc tgtgaatata agtctttatg    16500
tcaagctgaa cttttaaatc ttgataaaga atttattatt aaggctgact acaaacaaag    16560
ggaggaaagt gacaatggca aaaaagcaaa atcaaaatc aaatagtttt gaggacagat    16620
tagtggatct atatgatata gatgagccca caatattaac actttatgga agatctggtt    16680
caggtaaaac tactatctca ggaacactac ccaaaccaat attctttatt gatgtaaagg    16740
acaaaggtac tctatcagct agaaacaagc ttagagttaa aagaggagat atacaagtat    16800
ttagtctaaa gagttttgat gacatatacg aggcttatga ttacctatca gaaaacactg    16860
ataaatttaa aacagtagtt atagaccatt taactgcttt acaagaatta ggtaatgaaa    16920
aggtcaaagc tgaagaaggt aaggaccaga tgagccaaag aatgtttgga aatgtggcta    16980
attatatgaa agaggttata aacctttata aagaattaaa tgaggaaggt atactaccat    17040
```

```
gctttatagt acaagatagg ttagaatctg gtgatggtga aggagaagac caattaatgc   17100
ctgaggtagg accaggatta atgccatctg tatctaaata tttatgtgct gtatcaagag   17160
taataggtca tacttattta tatgaacact cagaaaaaga gggtatgaag gttaggaaag   17220
aaatccagta tagactaaga ctaggaccta acccttatta tattactaaa tttactagac   17280
ctcaaggatc tgaatgtcca gcttatctgg tacatgattt aaaatcacca acaactatct   17340
gggaggatat tgaaactatt ctggctggtg aatggaataa taagccagct aaatctggta   17400 aaaaaccag taagaaatct ggtaaaaaga aaaataaaa attttctaaa atacctttg    17460 acaaccaatt aaaaatctga taatataaac ttgtaaacaa agaggtacaa tatcttgaca   17520
aatatttatc tcataatgat attttaaaat ttaaggagga caataacatg gctaaaaaga   17580
ctactaagag aggtaacaaa aacaaaggag gattaaagat tgatctttca aacgttgaaa   17640
cttcagttac tatcccagaa ggaaattaca ttgtggaagt agaagatgta gaggttaagg   17700
tttctgaaaa tagtggaagc aattatttat catttacttt tgtaatagca gaaggaaaga   17760
tgaaaggaca aaagttatac cacatttgct cacttcaacc acaagcttta tttaacttaa   17820
aaggtgtgtt agttgcttta ggatttgata tccctgatga ggagttcgaa ttagatacag   17880
aagctctagt tggtttacaa tgtggggtag aagtatcaca tgaaatatat gaaggtaaga   17940
agaaatcaag aataactgat tttataaacc ttgacgaagc tgactctgat gatgacgaag   18000
atgaggatga tgactcagat gacgaagaag atgatgaaga cgatgagtct gaagttgatc   18060
ttgaagaatt agacaaggat gagctaaaag aattagctaa ggctttaaaa atcccagcta   18120
agaaaatcaa gaaggctaaa actgaagaag atctaattga tctaattgaa gaagaagctg   18180
acgaagaaga aatagctgaa caatataatg acctattcgg agactctgat gaagatgacg   18240
aagaagatga ggatgaagaa gaggaagatg aagaagaaaa tgactatgag tcaatgactt   18300
taaaagaact taaagctgaa gctaaggaca gaggcttaaa ggttaaaaaa ggaatgtcta   18360
aggatgacat catagaaatg ctagaagaag atgatgaaga ataaaattta attattaaaa   18420
tatgagggcc tttaaggtcc tcctttattt acccttggag gctactatta tgcttgaaag   18480
agatgtggtt aaatccataa tgaatatgct taaaaagaa tacccaggtt tttggtttaa    18540
aactcatggg ggaccatttc aaatagctgg cttacctgat atactaggtt gccacaaagg   18600
taagtttatt ggtattgaag ttaaacttcc tggaaaagaa aagaacctaa ctcaaaaaca   18660
aaaagacatt ataaataaaa taaatctagc aggaggaata gcttttatgg ctacctcagc   18720
tgaatataca aggaggagat tacatgaaaa atttagaaag acaccaacaa ttcctaggag   18780
aactaggaga tctgtatgaa ttaaagaata atctatatgg ggataatttc cacaagacct   18840
atcttgaata tggaaaccct gtcctatgta taagacttga agataagcta ggaagagcta   18900
aaagtttatt actaggagat caagatgact tcccttcata tgctgctcaa aaagaatctg   18960
tggttgatac tttactagac ttagctaact atgctattat ggctgctatg gaattaacta   19020
gtgatgataa ctcagaaata catgatctta gtaaagaaga atatgatgaa gaagacatag   19080
atgataatga cgatgaggac ttagatgatg atgatgacaa tgtttacgac gaagaagaat   19140
tagattttga tagtatgaat aaaagaatcct taaagcaata tctaaaagat aatgggggta   19200
aattccatag taaggcctca agagatgaac ttgtaaaact ggctaaggag gtataaggag   19260
gaggctttaa tgcctcttct ttttagtat gaagagaaaa ttatttaaac atcagaaaga   19320
agcattacaa ctattttaa gtaaagaaaa gtttgcccta tttatggaca tgggtacggg   19380
```

```
taagaccttg gttcctattg tggcccttga gaaacttgaa ggtttagata ctgtactaat    19440
attctcacct aaatctattg tatttaactg ggagtctgag atccataaat ttactaaact    19500
taaggaatat aaaatattta aattacaagg tagtaaaacc aaggttatgg aaacctatag    19560
ggctataaaa tcatactcag gattaaagat tattattgcc aattttgaga aggctaggtt    19620
gatggataaa taccttatga acttaaagcc acagtttatt gttgttgatg aatcccataa    19680
ggtaaagaat agaaatgccc agatatctaa ggctctatat aaaattgcta ctaaatgtaa    19740
atatagattg ataatgacag ggactcctac tcctaatggt tatgaagatt tatttatgca    19800
gtataaaatt atgaactcaa atattctagg agttaactgg aaacagtttg aggatgactt    19860
tataatcaag ggaggttata tgaactatga aattgtgggg tataagaatg aggaaatatt    19920
aaagaacctt atgcaccaga attgctatat agtaagaata aagattgta ttgatttacc    19980
agaacaactt cctgatctgt atttaacctg tgaactaaat agtaaagcta gaaaggccta    20040
caatgacctt agaaaggaaa tgatagcaca actagatata gtacaggaaa acattcctag    20100
gaagcaatta aaggccttat taaggtctaa tggtataccc tatgagggta atgagccata    20160
tgaggattta ttcttaagag ctaatatgtt tatcaatcaa ttaacagctg atcttaccat    20220
tacccaatat ttaaggctac agcagatctc aggaggattt attacaaaca atgtaggaaa    20280
tagtattaat attgataaag gcaaattagg cttattacag gactatctag aaggatataa    20340
aaagcctgtt gttgtaatat gtaattttct tgaggaaata aaacttatac atgatacttt    20400
taaaaagacc cacagagtag aatgcttaac aggatctact aagaatagag ctgagatcaa    20460
taaggatttt caggagggta agattgatat attaatacta caaataagtt caggtagtgt    20520
tggtctaaac ctcttcaggg cctcaaggtt aatattctat agttggaact aaaatatga    20580
tgattatgtg caagctattg ccagaattaa aagaatgggt caaaggagc cttggcaaat    20640
aatacactta ataactgaga atactattga tgagaaaata ttaaaatcaa tacagcttaa    20700
aagagataga gcagaaaaac tgttgactac tgataagtaa tgtggtaata tagaattgag    20760
gtgataaata atgagaaaag aacaacctag aataagtaat catactgaaa tagctaaagc    20820
tttgattgaa gctgggaaaa ctattaaggc cctaaccaag attaaagtca aggaggaaaa    20880
gaaaaaacaa aaaggccttg aaaggctaag acttctaaat gaggaaaaga agaaggagag    20940
agaattaatg aaagaatta atcctaatga gcctaagaag tcaagaaaga aaaaggacaa    21000
acctataaag agggttgatc tgaataaagt tgaggctaag ggaacttacc ctacaccttc    21060
tggaggtaat gcacctactg gaacagttga cttaaaaact ttatgtgagt cattaggatt    21120
agatccaagt aaagccaggg ccaagctaag aaagcaaggt gtaaacaaac catataaatg    21180
gtcaggatct gaacttgagg atattaagaa aatgttaaaa taagggagg tttaaaaacc    21240
tcttcttttt cgttgacaat atccacagta tatggtaata taaatattgt aatcaaacaa    21300
aaaggagaga actgaatatg aaagatcttg aaaaacttac aagggaagaa ttgattgagc    21360
ttgtaaagga gttatctatt gattggacag gagcctataa tagaaactat aagattgacc    21420
ttgaggagta tgagattgta tatattgatc ttaatgatct gaaagagttc aatgataagt    21480
taggtcatct agaaggagat gtgtatatac aatacactgt aaatcttatc aaggcccatt    21540
tacatcctga gaaggatata ttgattaggt ggggtggtga tgagtttgta gttatcagtg    21600
atatagctta taatctatgc aataccttga atatataccc tgagttatca tgtggctatg    21660
gtaaaggtaa acctattgaa gaagctatag tacaggccga ctcaatgatg tataagaata    21720
aaaaatctaa gaagttaaga tactcaaagg aggattaatt actatgaggt tattatggtt    21780
```

```
aaaagaatat ttggatatat gcaatatctt gggtattgag cccacaatgg aagcttgtgc    21840
taggtgggga aagaataaaa aactatcagg gtttttcatta acccccgtag gagcaactaa   21900
atagttgctt cttttttaaag cgatccgata cctagcaact ttcatgccaa aaagaaattc   21960
ggggttttct ttgacataga ctccagactc tggtataata atcttgtaaa caaaattaat   22020
tcaaaggagt tgttaattat gaataacaaa aaatttcaag aaactttaga acaattagag    22080
gaggaactag aaatacaagg ggtagaattt aatgatgaga atgacttaat agctgctgtt   22140
gaatacatca tagaatatga ttaccaccca gaacaatatg tggaagatac tttatgtaac   22200
taccctgaaa tgttcaagga tctataaaac taaggaggtg taaaaacctc cttttttattt  22260 ttcgaaaaaa tctggatttt tccattgaca tattctggag tatctagtat aataaaaatg   22320
taatcaatat taattaaata aaggagatgt taaacatggg ttataacatg aatgaaagta   22380
ttgctaaaaa tgtaattgaa ggaacactaa aaagaaaagg attaagatta aaaactgaat   22440
acttagaaat ggtggttaat caaattaagg atcttaaagg aactgctaaa agggataagg   22500
tacttgaact attaaagcaa aatcctgaaa tagcaaaacc tttaataaaa cctgtaccag   22560
gtggttatat aatggactaa gaattaggtg ggatctccca cctttttta ttttttctaaa   22620 aatctggatt taatcgttga catagtctgg gccctctggt ataataatat tgtaatcaaa   22680
attaattaat tcttaggagg aatgaagaat gactaaatta gaaatgttaa atgagataga   22740
aaaaataaat aaggtggttt ttgaaaagaa cttccaaaaa caattcttag ataagaagat   22800
agaactatta caacaaatgg gagtaactaa atattatata tgtaaacatc ataaaaaagc   22860
tgagattgaa aaatatcttg aggcttgcat ctgtgcaata tatgatatag gaagaagaga   22920
tgatctagga tggtaaaccc catccttttt ttcttcgaag ttttttcgttg acagatccag   22980 agttctctct tataattaaa tcataaatta actattggag gtaaacaaaa tgagagatat   23040
gatagaaaat caattagctg aatatgaagt aaaggaatta tacaatgagg ccacaatgat   23100
cttaggaaaa gcatttggtg taagtgctgt tgatctttat atagaatctg atgtggatgc   23160
caattattat ggtctatgcc atagatcagg taataaattt actgggatta caattaacct   23220 tttcccttc aggtttgcac aggaaggaga aaaagcttat gacaaaatca aaaaatttgg   23280
ttgggatatc aaggactgtg ttcttgaaac tatatgccat gaattagctc acttaactta   23340
ttggtcacat agtcctttac ataaaaaatt aactagcctt tattacaaca aagtgcaaca   23400
ggctagaaaa ggtgaaaact cagctgtagc acaaactaga agtgatatat acactttaaa   23460
agatttatgt gaattgatag aactagatcc aagaaaggca agaagcatat taagaaagaa   23520
taacattgag aaaccaggta aacaatggga gtgggagcaa ggtatgccta aagatatata   23580
tgatctatta atcaacttaa aggttagggg gagaaggtaa aacttcttct ctttttttcgt   23640 tgacatatct cgagagtgct ggtataatta tattaacaaa taacttagga ggtaaatcac   23700
atgatagata tatattatag tattcaagta gaagctgaaa acttctttgg ttgccaaaaa   23760
gaagatggaa gctgggtagc aacaggagca tttagtatac ctgttaatag cataactttt   23820
gaagaggctg ataaattatc caatgaggcc atagatggat ggttaaagga gtatgaggtt   23880
actaaggtaa taagtaggag atcacataca caagttaaat tggattggta taatagttat   23940
atcaaggatg atccattaaa gggtgatata attaataggg tgtaccctga tctttcagat   24000
aaagctaaaa tcaaatatgg ctttggtaag atatgggcta gcactatgtc aaaggttgct   24060
aagaaaggtt tacttaaaac ttgccctaga tgtgggggca ctggccatta ctcaagaacc   24120
```

```
tcagatggta acactacttg ctttaaatgt aacggcttta aatatgtgat accaactaag    24180
atctcaaaga aattttataa atctgtggag aaaacctttg acatctctgg caataactct    24240
tataataaac ttgtaaacaa aaacaaagag gagatgttaa atatgaactt aactgcaatg    24300
gaaataaaga tattaaatgc tatgagaaag aatgaatttg atgatggact agatgttgac    24360
tgtgtatggg tattctcagt aatagaaaac tcaggtatag aaggaactaa ggctagaggt    24420
gtgatctcat cacttgttaa aaaaggttta gtatttgctg atggagaggt aataggttac    24480
acagaagaag gaagaaaggt ctttgataat gctgatggag aagaatgtaa ctggggaggt    24540
ccaaaattat taaagaaat ccctgacaaa ccagaggaaa tctcttataa tgaaaatgta    24600
gataaaacaa ataagaaaga agagataaat gatatgaaag atttaaatac tatgaaagct    24660
gttgaaatta aagaattagc aaaggaatta aaagttaaaa actggtggac tatgaaaaag    24720
gctgacctaa tagctgctat ccaacaaatc caacaaccac aagaagaaaa ggttgaagag    24780
gtacaacaac cagctgaacc tgaagaaaag gctgaacaaa ctaaaattac tcttgatcta    24840
acagatgtta aggaaccaga gaaaaaggat gaaccaaaag ctgaaccaaa aactaaggaa    24900
ggtaagttca ccttaaagat gatacttgaa gaattaaata tgaatggtaa aaaggcaaga    24960
agaatcttaa gaaacaaaga agttgtaaaa ccaggaaagc aatgggaatg ggataatgaa    25020
gaagaattta aaaaggttaa ggacctactt tctaaataaa gtaggcccaa cctctatccc    25080
ctattgattt acaggaggat ctgattttct cttacccatt aactgcttcc atacttgatt    25140
accaaaggaa gctacagctg cacatattaa accttgtata aagccattca aaaaggtctt    25200
agctgtaaaa cctagttcca attgaattgc catatataag attgacaatg atatactgaa    25260
taccaaaagt attaatggta tagaccaatc cggtatataa ggcttagcct tgataaacag    25320
acctaaacag taacatgata ctatgattat taaaagctgt ggatcaatgt aattgaatat    25380
taaatttact aaatttttctt ccatgataaa tacccctaa attatctcta catattttga    25440
acttacataa ccttgcttct taccatggct agtattatat tctatatgat accaaccatt    25500
cttacttcct aatatagtaa ctctctcatt attaaatact gagcctatta tattaccatt    25560
cacatcatct ctcacattaa gggaagtgtt aaccttaact attccttgtt taatatcctc    25620
atagaacttc tggctttgtt caccctcgta acgaacgtat ccatcagatg gagtaccatc    25680 cttctctataa aatgttattc ttaaccagcc attagttcta tacattggac tagccttttg    25740
accgggttgt aaagtctcat cacagtcagt tacattcaca ttcttttggat cccaccacac    25800 ataagttact ccattgtcat tttgatactt catgtggtag tcaaaactta atctgctgta    25860 atgtttatg tcaatataag catggtactt cttattcttt ccaggatata caacttctat    25920
gaaatttcta gaaggatata ttccaaggac aaataaatta tctaggctat caataaatct    25980
accagggact ggcttacaat cctcatctag aacttctatt gaaccttccc ccactaaagt    26040
agcattagtt cttgtctcat tagactcata gaatccttta ggattattat ctgctggaat    26100
gcttggagta ctacctccac tgatctcctt attacaaata cccccagcta ttaattcacc    26160
aataagttta gggcctttag ccttatagat acttacatca gtggttgctt cacagaagca    26220
tacttccact atgacagctg gcatagtagt cttttcttagc tcatataatt tagcattaca    26280
tttaactcct ctattcttta atcctgtacc tttggcaaca gcattaacta ttcttgtggc    26340
atatacttct gcttctcctc cagtgccata tatccaagtt cctgtaccta aagcaccttc    26400
atacatatcg taagccttgt caaaatgaat actaataaat aagtcagctc cccaggcctc    26460
agccttatta acccccatatg ctaagtcagt gttaacatca caatttccag gagtgacatc    26520
```

```
tagaacacta tggccttcat ttcttaaagc cagtatcaca gagtctttta cttttctatc    26580
ctcagtagtt tcatcaatta aaccataagc acctttagct tgaaagttat gtccacctct    26640
tactgctatc ttcataataa acatctcctt taaatattat agtgttttat tgggcctgag    26700
aggctcgcta cagcatttta accacctcct taatatattt tcttatataa aacctaacag    26760
gccttaaatg acctgctagg cttataagtt aacctttgtt actaaatagg tgatctttta    26820
tagtatctac atcctctttg atatcctcaa ctacattgaa tttatcaact agcttatcta    26880
tcacttgatt taatttattc tctctttctc tagcctcttt tctagtgtca tataatagcc    26940
atacaaatag actacaaaag ataccttggc taagaacttg agttagtagt tcttttccca    27000
tagattacac cctttcatta aagtcttcac cacatattct tttatagtcc tctggtgtaa    27060
tttctccttc tggattagaa gagcatttta ctgcctgatg taatttgtcc ttacctattg    27120
ctccaattct ataagccatt tcccagaaat tcataatctc tacctcctta tttattcatc    27180
aatttaattt ttatatcagc tagttcttgt gttaatactt tcattatggc cttagtttgc    27240
attagctcta atttggtatc agcaagagcc tgagcttgat agccaactac tttattaata    27300
tctagaggat taggatctat agcctcatat gaagtaaata ggtccttatc tttgatactg    27360
tatagatctg atctctttt actaatatca aatttagttg ggccactctt tatgtggtca    27420
aatagactta cagtcatttg tataacagga agattgtcta gatcaataac ctcagtgtta    27480
tccacaaagg ctaaatgccc ttgtgaatta tgaggtatat ggagacatat aatatcttct    27540
atattattta atatttcact atcttcccta tagtatagag gttcaggcct attaattagg    27600
tctaatatcc tagtaacttc ttcatggtct ttatctataa atgattttac atcctctgag    27660
tcttctgcct gatttatcag ccttctttt tcatcatcat agaatataag gtctataacc    27720
ttattagttt ccacagaata attaaatcct actattctca tgttttatca actcccttac    27780
tcagtagcta aataggttag tattatttga gttggcttac cagctaccat ttgataacat    27840
ccaccattta aatatgagtt agtccaatgg tcaatagtac aataaccaga ggtattatta    27900
gaagcgtcat tatagttatg tgatactaga gatataggta ataccccaatt ccaatcctta    27960 ggaaaatgta tagtataact tacacctccc cctgagttag cataacctgt cttaactatt    28020
tgacggacta atcttagtcc tcctcccaga ctaactactc tggtattatc ccctacatcc    28080
caatagtctc ctttagccac aggactatct tttacataga ggttttccac atttcagta    28140 tataatcctt ttccatcttg tttatagtag aatctgccat cttcagatcc accataccag    28200
tcatttattc tcatatattt tctggcccat aagttttcag ctgagaaatc ttgccagcat    28260
tttagagctc cactaataga ctctaatcta gtattaaagt ctttatttgt cccaggttca    28320
tggaagtcaa tcattctacc tacttccata acaccgtcat gaggtatgaa aggaatgcca    28380
ataaagttag tattgccttc agctaactcc caattcttaa atttattact attagcagct    28440
gtaccatttt tacctaggta agcactatca tggttgtggt tcgaatctgc agctcctatc    28500
tcagagggtc taggtttgtt gatactacca tataatttat tccactcagt ccaatatccc    28560
tgattattgt agaacctagc atatactaag ccagcactat taataaataa ttggttatat    28620
tctccaccct ccttactcat tgatagaaga gttccatata tacttccagt gtgagggcg    28680 ttgggtatat catttccccc tactataaag gttcctggag atttaatatc attaaaatct    28740
aaaaccttcc ccttaatact ttgtagatat ctatcatcat gggtatggtt agttggggat    28800
gcccccacat ctgctgctgt tggtttatta tcctcatgat agatcttctt attgttctta    28860
```

```
ttaacaatat ctaaagagtc tatctttaca ggccttccag catacccctat atggactttg   28920 ttatctgcat ctatatacat cacatagtca tcactaccct ctttagtcct acagctaaat   28980
ccataattgt gggccccgat aaatttctga cctggtctca taattaagtg gcctgataat   29040
tctccaccag tagtaggtaa ggcaccaatg tcttggggag taggtttgtt ttgtttacta   29100
tatatttcag cccaagtcgt ccatccagta ccctccatgt ttgtagctgt tctagtaaaa   29160
actcttccac catctgcaaa gaacatttga gaagcccagt gtcctgtatt ccaggataag   29220
acaatcaatc tcccatctgc taggattggg gcatttttat cgacagaatt tctaactgta   29280
gaataaatac cccctccgt aatggtgttt agatctacac cctctagtct tttggctgtt   29340
ttatcccagg caccaatgtc ttggggagta ggtttagccc cagagttata atcctttctc   29400
caagggaacc aatccgtatt atttacttta tatctccaat acttattacc attggtatca   29460
taatactctt gccatatcca gttattagta ttattatgct tagtctctgt actaacatat   29520
actatcagta taccatattt tgtacccgtt agtggggcat taggtaactc acctgagatc   29580
agatattgcc cctcagttaa agctgtatta aaatcagtta tggcgtcctt aggaatggga   29640
taagccccta tttcttgagg tgtaggctta ttagcctcat cataaacctt ataccactta   29700
ctccaagaat tatttcctga tgtgtagttt ctaacatatc tagttatttt attggttgga   29760
tataggttaa taaactcctg ttggaatccc ctctcacccg tatttctaac tataaaaacc   29820
ctattactca tatgggctaa ggttccctcg ggggtatttt taaagtcacc tgttcctgta   29880
tcaaagtaga agaaggcatt cgcttgttta aaggaattac aatctctatc taagggagca   29940
ctaaccttaa taagtgcttg atcttgatta gcctttcggt ctatttgatt ttgtaaacta   30000
gtgtctttct caaatagtag gtctaatctt tttagcacat cctcagggc tagattatag   30060 tcaggtacta cattacctct agctagtaat aggtttagta cctttaatga tgtgcttgaa   30120
gttgcacctt gtaccacaaa ctgtattttg gtatcagtag ctccggaagg aatactaaac   30180
ttatgagttt ttgatttgta cccattactc tgtggtgtac taccttgctt tataatactc   30240
ttatattgtt gacctccact agtgtaagcc agtttaattt catagctagt aaaactacct   30300
tcaatatctt ctaagaaggc taatacataa tcactatttg gttctatagg cagagttta   30360 atctcaagag tttgtggacc tgttgacata ccagaccatt taaaacctcg tctcttggtt   30420
ggagcatctg ttatgggtgt gatattacca ggaccagtat aagactcaga gttgtaccac   30480
tcaagcctat taatagtacc aaccctcaaa gcatccagtc tatcctcatt agatttagac   30540 ttctttcta cctcagtcat tttctgttta tgttcggtag caaagttctc aatgttttca   30600
ttatccttat taaaatcagc cattttggc ttatctgtta actcccactt attaaaaccct   30660 aaagtaggag ttttaccagt acttggcatt ttgcataccct cctttattca gttatagcat   30720
attcttccca tttttccccag gtaaggtcta gactgtccca cttgctccac atataatcat   30780
atctatcgaa catctcccaa gtaatataaa gtaatataat ttgatatatt aaatgagcag   30840
gcattctttc cctgaatact ctttctagag cctttaggtt aggtggtacc cccggtaggt   30900
cagtaaagct aattttgatc ttactctctt cagctatgaa ctctaccttt acctttccac   30960
ctgtgtaggc cttagtaaga ttttttgatag atgtactatt aaacttttc caagcagata   31020 gaactactgt aataaagct cttttctctt ggtcagaggg tgggtaatca agtatttat   31080 ataactcaag atcagtgaaa aatctttcta gaccttcctt aggagtggtc ttgggatcca   31140
catagtcttg taattcctgt ccctagtat atagtttctg aagttcagta gccataatag   31200
tgtttactaa gttatcagcc tcttttatat tatcataaaa ttcaggaaca tacaatagta   31260
```

```
attcttttg aacctgttct agactataca taagttacca ccacctcagt aatggttggt  31320
atttgattag caggaatagt taaagattga ctacttccat taagtgtaat ggttgtataa  31380
tcttctactc cctcaatatt taaaagcata gcccctattc tatttataga taggctagta  31440
attttaaata cttgactgct tagaaactct tctagttctt tcttgaagtt taattttatt  31500
tgttcttctg taactgaact caatttctta acctgagctc ttacagtgat attaaaggtt  31560
tgggctgact caacagtaaa aacacatcct ataggagctt taccctcacc taaacctttc  31620
ttgcctggat ccatgtattc ttgaacttta ttaactagtt caggattggc aggcttattc  31680
tcaactgtgg ttataatacc cttagcagta tttatcccat tccaacaggg aagaaccaca  31740
gctttaccta ctccagctac acttttacac caatctgtta actgttggac atttccatct  31800
ccagatggtt gtatagtggc tttagtagct ctctctctta actcatcatc tgtctcttga  31860
tctctaccaa taacaaggat atctcccata gtagcactct taagttctgc tatagcattg  31920
atgggaatta gatgtgtacc tgttgatact ttattaggtc ctgaacctaa agtctcacat  31980
tcaataatat tgggctctat cacttgccag aaataatctc ctccttggaa tcttgaacca  32040
acatcgggtt catagccaac aaacttagct gaccttctac acttagttgg aattattctg  32100
gatatcccta cattggcagc tctctcatct aagaacttac ctgtagcagt acttagaaat  32160
actgagtcta atatttgatt aacattaaca gcataaaact cagctagctt aacagcaaaa  32220
accatagcca tatcataggt gaaacttcca gttctagtgt caatatcatc gggggatagg  32280
cctatcatct cttctaataa ttctttatgt gttcgggaga ataaatcttc agaaaatccc  32340
attatatcac cccttccagt tttgtatctc catatatggt atttatccat acttcaatat  32400
atacattctt gccttgcaca ttatacttta gatcagttac tttagtcact ctatcgtctt  32460
ctaagagaca ttcagggata gccctattaa tctccatttc aagaagttca ggagttacta  32520
gagagtcatt aatcaaagct ctaatatcac aaccataaga agtatcttga taaatcatat  32580 aggcatttt aggagttatt aatctttat ataaagattg ttttaaggcc tcaagaccat  32640
ccacattatc ataaattcta ttaagattta gatctagttt ataggtcttg gtattctcca  32700 ttgtttctc atcaactata agggtatctt taaagccatt aggtagcatt atatcaacct  32760
cctaagatcc ctaacataaa atatctttgt ccatcatcat agggcataag atatacagta  32820
tcgccctcac taatagactc aatatgtttt ggaacatcta taatatttcc agatagtact  32880
aattttctat tgtgaagaca ctcacatttt aaagggctag tactaagtac cttagctcta  32940
taaatattta gagggtgga catattacta tatacttgtt ttacacagtc taataaatta  33000
ttagccatta aatatcaccc tcctcagtac atttaagttt taaattcatg gtatagtcag  33060
tatcaaattt atgggtatca gactcaatat agaaagcctt attaatttt aaatgggta  33120 tactaaccac aatggctttg ccactaatac agtcaggtac acctataaca gttatagaga  33180
tatcagtttt aggtctctta cctgttctcta gctttattct agccttctca tttaattggg  33240
cttggtttag ttcatcactg atagtatcgt ataattgaaa tacaccatat ttcttttggc  33300
tgctatcatc tttagcagag gcaaataaag taatctcggg atcatcttta cccttaccct  33360
gtttatattt acatactagc tttacctggt tgacaatact atcaaagttt ctacttcttg  33420
aaaaagttcc aatattttta ccatattcga atttccacaa ttcgttattg gttcttcggt  33480
ttataaaatc aaacttacct gtaatagaat tatagtaaat ataaaactgt tctccagttt  33540
gttcataaac ctctttatt accttcttca taatatcata gggagtttgt ttctcacata  33600
```

```
ctaaactaga gaaagtatat ccagttttag ctactactcc aggggtaacc ccaaaggctt    33660
tacataatga ctcaaatata gcttcgccag tttggttttc gaatacaaag ctatctttat    33720
tattagccca ataaatcata gggtcataag cttttaacctt aagtaaatgc tttttctcat   33780
tatctgagat attcataata ataccattaa agatattctt accctcatgg actagtacta    33840
cctgatctcc atcataaatt ggatgtatat cttgagcatt atattggaat gatagggtac    33900
gaggggcaga tgaagaagac cctgcccaac tcttaccact ggaggtattt gtaatatcaa    33960
aggatttatc tccttgtacc acaattaatt gcatattata acctccttat ataatcacca    34020
gaactccaac cttctttata tcctgaacca ttatctaatt tatactttac ataatgccat    34080
ccattttgag actttaatac tgtaaagtgt tcattaggcc atatcttacc cttggtagga    34140
ttattgatac caggtccagt tcttacccat agccatgagt aaacattagt agtagtagct    34200
gcccaaggtt gagtacctcc agaagaacta ccacctgtat taccactata ggctagttta    34260
ggttttggaa ttgtgaaact aactgattta acctcaggct tcttatactc agttagtttt    34320
atttttactt gaagagtacc aatatctcca cctttctcag tatatgagat attatcaata    34380
gtaactaata aattaatatc agtactagta atagtaaacc ttactggatc tttacccatt    34440
tcaataagtt tagcataact tactcggggg tctgcaatat cagtatactc acatccatcg    34500
tagtatgagc ttggtaactc aaaattaaaa gaaaaagatt ttagcttagg gtctcctatg    34560
aaagagagtt cccctaagcc ttcaatggaa actgtactat tatctctact atcagagata    34620
tttatatcag tgggatttac tggtaaccta aacctagtat ctccctgtat taaccagaat    34680
tgatatttac tatgcaaggt ccagttcacc tccctcgaac atttcctgat ttaacatttc    34740
cacaataaat ctgtatactc tcattaattc actttctgag attgttccat cttcagcctg    34800
tactgtgaaa ttaaatgagt tgttaatgtt cataacttta gatccatcat cacttcctgc    34860
tccagattgt cttagtaaat cctgagtttt atctgcaggt aatacttgag agcctctagg    34920 cattttgag aatgtaggac ccataactaa ttcggggcca gcttcaccaa ccatggcagc    34980
tttatcagtg aagaaatcag taccttcagc aagcattggt atctgtggaa tattgatacc    35040
tttacctcct atgattggaa cccagtctgg tatcttaata gtattaagag caccaattaa    35100
tccattgatt aaactgatta ttccatttat aggtccttta gcaagagcta gcataccatt    35160
gaatactcca ccaaatatat tcttaactcc ctcccaagct ttagaccagt tacctgtaaa    35220
taccccagct ataaatgcaa ttataccact tagagtttgc attaaagctt gaagaatatt    35280
tgagatattt tgtacggctc catttacagc cgcagcaatc attggccaaa cagcattaaa    35340
tactgctcct aaagcataaa gtataggagt taacatatcc acaagtcctt ggaatatcat    35400
accaaaactt tctatagcag attgtatatg gggaactaca ctctcagcaa agcttaagaa    35460
cattggtaat agtgtattat tccaccaatc agctaatcct tgtaagattg gcattaagat    35520
gttacctatt acttccacaa cttgagaaat tgcaggagct atataagtag caaaggcctc    35580
agctaaagaa gtagcaattg gcatgaaaac attagttatc aattctccaa gagctgtaaa    35640
agtagcagag aacatagaac ctaatacttc taatatagga cctaacactt ccaatacagt    35700
ttgccatact tgagtaaatc cttgaacata agaactact aagtctatgg ctggaattag    35760
gttattcata aatatagaag ctaaagttcc aaacatatca agaagtactt gacctatagg    35820
agctaatact cccatgatag gctcagctaa accactaaag gcttcttgta tattattgtt    35880
agcctctgat aaataatctg gtagacctac taagatctct ccaaaattat tatatatgtc    35940
ttctccaaga ctccatatct tctcattaat ttgatctgcc acatcatcag gtaagaactt    36000
```

```
atataatata tcattggtta gatctataaa gggttgcata gcatcccaa actcccaacc    36060 attcatgatg taatatatag tctctcctaa accttggaaa gcagaaacaa ccattgagaa    36120
tatgggtcct agcttttcaa agccctcttg tataaatgtg ataccattta gaacagcatt    36180
agctataacc tcaacggcag gggctagggc atctcccaca tctaacataa ctacagcagc    36240
tttggatttt attctctcca tggttctatt aaagccctta tccatttttt cataggcagc    36300
ttcagtggcc ccagcactat tcttcatctc attaagagca ttagtaaagg cctcagtacc    36360
ttcaccagtc aaggctagtg cagctgaacc agcttctaca gaaccaaaga ggtcattgat    36420
acccagatta cttttctggg cgtgttttc taacatctga agggcctctt gtatattacc    36480
tccaccttta atgaagtctt tgaaaccctt accagctatt tcccggaaga ccttatcagt    36540
cttggttccc gatttagata gctcatctat agcagctctt atcttagtag tagctacaga    36600
tgttggaacc ccctgagctg ttaatgcagc tatagaggca gatacttctt caaaagatac    36660
cccagcagct gaggctgaag gtagcacatt gaatagggat tgtgatagtt gctcaaagtt    36720
agtcttacca agtcttactg tagtaaacat aaggtctgag gccctttgaa catccatatt    36780
cttagctcca tatgagttaa taacagtagt tagtccatca accgcagttt ctattgaggt    36840
gatacctcct atagaagctt taccagctgt ttctaagaaa ctaaaaacgt tatcctctgg    36900
aactgatgag gatatggctt gataaagagc aggtactact ttatcaggca atatccctat    36960
atcagaactt aacttttta cctggccgga catcttatca aaggtctctt gagtagagtt    37020
gggtaataga gtcataacct catttaaacc ttgctcaaaa tccccaaagg ctttaacact    37080
gtccttagta aaatcccaga cagccttagc tgagaatact ccagcagcta ctccaccaat    37140
tttggcaaga gtacccatga aggaattacc actatcagcc atctggttaa atgcaccaga    37200
gatcttatct tgggcagaga atatggcagt aaatgcagct tgacttgcca ttatatccct    37260
cctttatgat taagagcctt tcttttaactt atccctagct tttttatctt cttctaaagc    37320
cagttcacat gaagctataa gaaaggcttt cctattggga gatagtttat caaattccca    37380
gggtagtata ttatgcttct ggaataacac atgagcccaa aatgcactag tgtcggcctt    37440
tattagtttt ttgcttcttt gattagatca tccttattat cgcctaatcc atttatgtcc    37500
ataacctcac tagttatcct agtgaaatct cctggtaagc ttagtacatc cataagtaaa    37560
tctactggat ccacaaactt agtagactct aaccattttg gatctttaaa gtcagggaat    37620
actatggttt ctagtatcat ttccctagta gctcttcttt ggtctgttat tgagttagtt    37680 ataccttgt ttctagtaat tactgtatt tctcttttgga tatcttccat ttgcttagta    37740
gtgattggct ttaatatcca aggtataggt tggcccgcta attcatgacc ctcagggaaa    37800
ctaaatctag ctaccccttc aacttcaatt tcgggtgatt gtttacctt atcattttcc    37860 atgaaaaatt ccatactaaa ttttgacata ataatctacc tccacaatat tcttaatctt    37920
ttataaatat cttacttctg aagctgagaa tgatattct tcttgaattt cttctccctc    37980
agcatctagt ccaattagtg gtaaatctcc ttctaattgt actcctagta attgtactct    38040
gtcctcacca taattcttaa catagtcaga atctggatca tcacatacag cttgtatatc    38100
catcttaggg aatataccag tttttaagta ttctttaata gcttctctta tcattggagt    38160
agctttgaat tgagttatag ttccagttat atcataacct ataaccttg aggttaatcc    38220 tttctgaccc ataactcttt tcttagtcac ctcaggagta aatagagctt ctagttttat    38280
taagctagtt acttgcttac ctgatacaaa agctctaccc tctctagcag acattctatt    38340
```

```
aacttcactc atgggctata cctccttaat tattcttaac agttacaaag tatttcttga    38400
aagttcttac aggttgtgta agtatagtag catacatagt cttcccttta ctagcttctt    38460
catccaccac tacatcagag tcagggtcca cattctttaa tgctccttga gcttgtagtg    38520
tagttaataa acttattagt ctatcctgag ctagttttat accatctttg tggttaggga    38580
aaacattagg aactaagatc tgagatccta gatctataac agcatccaat acagccacaa    38640
ctttattatc tgtaaagctt tcatcccatt cttctgtaaa agtatggtgt gtatttatat    38700
cttcctcaac tactaccttt actctttcag aatttgagtc agtttgagtt gagaatataa    38760
attgacctgt ttttaatcca tcaactattt gagagtgttt tagtcttgga ttagcatcta    38820
ctgctccagg atatgcttta taagtaaggt cttcagtata tccagctgca gctctagcac    38880
cagctaccca tgcagttgct tgagaagctg ttaacttagt gcctccatcc agtacaaccc    38940
cattttaac attgatgata tatgggtaat cacaagtagc aaagtcagaa gtaactgcca    39000
caatgttctt accaacctca tctctgaagt atttaagttt tgataataga gcagtgtgta    39060
attcactctc agtaaatggg aaggccatag ttttaaagtt gtataactca cagttatcta    39120
agaagttaat aacatcagag ttattcatct gagtagaagt accggtacta aactcagtct    39180
tagcagtctc atctatagaa ccacttccac ttactgtaaa ccattgagac ttaactgttg    39240
atatttcagt tactcctgta gcctcaaaga ttttagatcc ttcaagatat aataatatat    39300
cctttcctcc aagaggattg gtcttaatag ttagagataa tttattaccc ctttctccag    39360
ctttagtagc tgtaaatgtt agagaccctt ctacagcttt ggctttagtt ccacctgtta    39420
agttatatac taaaacagtt gcagcttctt ttaaagcctc tttaactagt aatacagtag    39480
ggtgagttat atcataccca agttgatata atgcttctag gccaccttca ttggttacct    39540
tgataacatc tccagcatta ccccacttaa gttgtaatgg taagatcata actcctagat    39600
tattaagctt aggctcatta agtccaccac ttacaaatct agtatacata ccaggtctta    39660
ctttattttg tcctggaata aaagttcctc ctgccatcta ttttacctcc ttctttagcc    39720
agtcttttat aatctgacta gtttgttttta ttgttaactc ttcatcaggt ggaagggatt    39780
gaactgcagc gttgaagaca aactcctcaa cctggaaaag ttgttgacaa tgggctctta    39840
attgaggtat ggaaaatttt tgtactttca ctattttacc cccttttgtta tctcaaagtt    39900
ttcgaagtaa gttggatctt tataaagact aaccacaata tcatagttta tctctacctg    39960
agaatcttct tcagtttcac cttcaaatac ttccacattc tttatttga gattttttgtt    40020
ggtcttacta ccatccctat taagtatagg aattttttcta tttctcaagt atatagcatt    40080
agctatattc tgagcaattt caagagagtc tttaggttca aataccttaa ctcttaaggt    40140
attctcagtt ctataactac aaagagtatc attctgagga ttaaataccct tcttgaaata    40200
taatgaggga tacttgaact tttcaggtat tcgctcaaaa tagagggtag taattccagt    40260
tagatcagat atgaatttag caatactccc tatatctgct gtcattaata actaccccct    40320
aaaacttcgg ctaaccaatc ttctagtttt cttttggaaag cctgttcaaa tatttttca   40380
tatatttta ctgcattgtc ccaataaggt ttaccaggta cttttctttg tcttagtacc    40440
ataccagtct tagctcctgg ttgataaata aatttatctc ctgaccatat gccaggaacg    40500
aatctaaatg attgtccttg tggattagta tagtgaccat cgtttaccca cttagcatat    40560
tttaggttag taccaacttc taaggttagt cctccatcac tacttaccca tataccattc    40620
ttacccccctt tttgaaagga gttaagtaat aatctagtgt ctactacttg tagtctaatt    40680
atttcatctt gaaccacatc aaggaagtct atccctgcag cttcaaacca tactgctaat    40740
```

```
tgcttttga aatcactatt agcggcatct cttagcttct ttataaacct ttctatttgt    40800
ttagcatcta tttctatgcc tccagaattt gaagccataa ctatctaaaa tccttagcct    40860
ctataccaac cttaattttt agacctctta tatccctagg agctttagct atatatgtga    40920
taccagtctc aaggtccaca attttatcat tttgtctaac atcagttcca atagcaaaat    40980
ctactgagta ctcctgggta atcttaaacc taggttcttt gtactcaagt ttttctagag    41040
ttcctgactt aaaatgacag ggtacctcag ttatgtctgg ctcatcagga taactaaagc    41100
taggggtatg ggctagccca tatccgggat cttcaggatc ttctaatagg tggtatatat    41160
tacatctatg atttaagagc ttgttatatg aatttctaat catattacag tacccttaat    41220
ctcatagtag ttgttctgat agatggacta tcatcttcta agaaaggttt aatcagaggc    41280
ataatatcag gctctataac agccttatca gttcttcttg tatatgagta gtcatcatag    41340
gtctcggatt gaatatcagc cttgctaatg accaaggatt gtagtccata atactcagca    41400
tacagtatat gggctaacct taattcttta ctattgggat ttttctccac aatagtatca    41460
tagtctttac ttgaattttt aaaaattcct gagatcttgg ctttagctct taatatatcc    41520
atctcaatat ttttggggtc tcttttccta atctcaggat tacttgagaa gtcaattatt    41580
tcatccggag taatattcat atgagccacc cctatctgtt tcttttattc ttgtttgtaa    41640
atcttctagc aggttcttct ttattgtcat ctgtagaagg tacttcttct tcagtaaaat    41700
cttctagagg ttcatcctca acaggttcat ctatgacaat cacatcatag ttctgtttta    41760
aataatttac tagactatct ttaacttctt ctacatggtc ttgggtaatc ctatgaccct    41820
taataaccag agtttgtaat ttacccttttg ctaatttgac cttagccata atatctctcc    41880
tttctaatga aaaagagccc acatttaaag tgggccttca tgattaagct tttactttaa    41940
ctatcttagc agcagcttta ggatcttcaa acttaacatc catcttaaga gttaaaacta    42000
cataagtaga tctttctcta ggagctcttt ccaactctat tctgatatct cttgagatac    42060
ctataactat attcttaggg tgagttaaga ttatgtctga tacttgagta gaagagtcgt    42120
cataatcttg tagcatagct ataccttttaa caggtactcc ataagcagat ttaacagtac    42180
catttataaa tgagtcatcc ccattagcag ttaatctttc tcctactaag tctacccaat    42240
cagtttctaa accatttgag cagtagaatc tccattcacc tgggtttctt aaatacttag    42300
ctggtacagc tttcttagct tgttttaata ggtctttact taaagcagct ttgttagcat    42360
ctactacatg agcagttaat tgttttctaa ccccatctaa ttgttgtaag aaagtatcgc    42420
tactatgtcc agtatcacca tttacaatta tttcttccat gtcaagagca actctctcag    42480
ctaataattg cattacagtg gcttctattg attttccttc tatatttgtt tctatagtat    42540
catcagttaa cttaaccaca gctataaact ctttagcttg taaagtaact gttccagtag    42600
ttggagctga atatttagat tgtcctggat ctgttccttc agctgcagga tttaatactc    42660
tttgaccaaa tcctattgac tcaatctttt tagagtctcc tttcattggt acagttctag    42720
cctcttttaa tattgttggc tcatcaatta tcatttaat aaaagcgtta gcttgttctg    42780
gatttaattt acctccacca tttaatacgg cagcgttaaa tacagcttta tttacttttg    42840
acataacttt ccctcctaat tgttattatt cttggtttcc accaaataat ccattaaata    42900 ctgattttg aacttcttgt ccttcttctc cgttttagc aatttgttta cttcctacat    42960
atggagccat ggcttagct actgcctcag ctatttttc ttcctcagtt ttttcttctt    43020
gtttctggat taagccagcc tctaacatag cttttccac agccttagca actatatctt    43080
```

```
cagtagtagc tggttgacct tcattcttat taacttcacc ctcaacaggt ttagttccat    43140
ctaatgcctt tttgatagct tcgtctatca tttttttgtac ttgagtttca ttcatctctt   43200 cttcccctc cactgagtct aataattcat taatagcact ttgtgctgtt tttaactttt    43260
ccacattttt tgaagatatt ttcttacctg ccttattgac tggtaactca aaagatttag    43320
ctacttcttc tggagttcct aataatattc cctccatagt ttcagaaaat tcttgaagag   43380
cctcctttat cttatctaca tcactttcaa aagatctagt gtaatcccaa ctagaatatg    43440
gatatagaat atcttctaag gtactaactg cattccagaa attatttctt tttgcagtct    43500
ctttatattt ttcagagtat gcacctttct gtatatgctt tggagttaac cctagggcct    43560 ttccaattt atcaagtata gattgaccta tagacttctc aatctcatca atatctacat    43620
cttgtgtaga atatttacca gtaccaccca tagaccatcc agtaatttcg cctttctcaa    43680
tcttgctcca tagatcatca tcgataatct cagctttagc taaccaagtt ccagctttaa    43740
ctactgtacc ttctattgtg gtatcttcct cagttaccca tgattttaca atcttgacac    43800
cctcaagagt gttctcattg tgttgtaaat cactaccaag gccattttca ttaaaccact    43860
cacaagcttt tttgatctct tcctcagtca taaaattatc atggtagtca gcagtcattg    43920
gctcatatac tacaccgata acaaaatgat tatctccttc agactcagac tttaagattg    43980
gcttatcata tctaaatcta ttaggagctc caagttcttt agccacaatc cattgccatt    44040
tattagctgc tttatcaact aatgaaaggt aatcaatttt agcatctgag atctcaatag    44100
ctttcttaac tgattttact ggcatttact ctccctcctt tacaaattat attctgctat    44160
cacttgatct ctgatagctt ctttttcttc tttagataat cctagtatat ccttatcaat    44220
tacaggccca tgagtacaat gacaattcac agtctcagaa gctggtaagt tgatatccct    44280
aggaaatcta gcttcataaa ttcctacagt gaagtactca cctttattaa tgacagtacc    44340
atccagatcg acatggtgtt gccttgggtg aataccccct ccccctgagt gtttccactg    44400
tattcctgtt actgcgggc attgattaaa agcctcatcc ttagcatatg agtgggctct    44460
taacatttca gtaatagcag tagctctagc tctagttcta ctaaagccat aagtctcaga    44520
taatttacca actacatctt ctacagactc tccatcttca agagccttat ccagaatatt    44580
ctgtagtttt tcatgggaag ttaatttcat catttcccca agtttagaag accactcatc    44640
tataaaggta gtagtatatg gagaaaaagac tttggttagg gataagtcct tatcaatacc    44700
ttgtaaataa gtatctccta aattttctat agcttcttga taacaactct taagagtttc    44760
tgctaaagaa gtatcgatat tatctgtacc tatttgagac tccacatatt ctataaattc    44820
ttcaatggtt tcaaagtctc catctttat aagatgtttt aattcttctg taaggagatc    44880
agaaatagtg tcttctaatt cagagatctt ttctattgta taatcaatct cctcatagcc    44940
agcttctttc aattctttct taaggctatt atcttcattc tttaagatct tatcaattt    45000 agcgatcaac tcatcagtac ccactattac ttacctccctt ttaattgata gtttaataac    45060
tgtttcttag cctctttaag tacagctatc acctcatcac tcccattaga gttttgagcc    45120
ttctcaatta tacttgttaa gttattactc atagaagagg caactgagta agtagggata   45180
tttgcccatt cttcatcaat aggagtatag tccttattga ttgatgaata atactcctca    45240
ttaatctgat taggagtcat agctctagag gctatagcaa acattccttt ctgataatca    45300
gagttctcaa tattaggact cttaaagtaa gcttccacat atttaaaacc atagccagat    45360
agaataacat tatttagtat ccatgttagg ttttctcttt caggaacaaa tacttgctct    45420
tcagtttttc ttgtagcctc tctggctgta gccacattat aatcttggga gtaccctaca    45480
```

```
tatatatctg gtagtaagaa agaagattgt atcttttcc tagtattatc catgtagtct    45540
tggaataact catccttctg taatatttca gatagggct tgacctcaac agtaactggc    45600
ttagagtcat caatggcagt gtctttctct gcagcttcag tttctagtac taagaaacca   45660
tgctgggaat tttcacctt tacactattc atgtactcag ttaactcatt ccaagattta    45720
tcattaagag taccaccttg aattagtaac attaatggag tatgtttacc attagtaaaa   45780
tatctccagt ttaataattc ggcctttctt gaaccttgag cggctaacat aggaccttcc   45840
catcttggtg taccatagac accataacct gttttaaaat gaagtatact gttagctcga   45900
tctttaagag gtatctctcc cttttcataa tactttccag tattcatatc tagatctcta   45960
ggatctcccc attccttaaa gaagattgat tgattattta cagtctgctt aaatcttctg   46020
aaccttttc ttctagtgta ctgtttacca tatcgggtta cagtgtactc tgtactctca    46080
tcatctagct taagaatttt aattgtctta gggtcttcaa tttctttat ctcttttacg    46140
agagctgagt cttaggatc ttctacgatc tctaaaaaag aatacccaag tccttctctc    46200
caatcaacta tctcttcaaa gacattcttg gttggtttat caaaagacag ggtatcaatt   46260
aattcttcca gctgtttata ttcagcttc atttctggag taggttcatc taccttctca    46320
atatacctaa tacctattcc gaatccagca atattattc ggtaggcctt tttgcattgg    46380
ggtattattg tagactccct tataatcact tctaatagtt ggggtcata ttcaggagat    46440
atctcatcaa cttcaattcc aagtacactg gtttgttgat tagatttatc cactggatcc   46500
aaagactttt ggatagggtc tccacatata cttctggcgg atatcttttt caaagttact   46560
ttacctcctt tcttacatta tatatcaaat tataaaatcc agatggcctc atatttcagg   46620
gaggattaca tcaactccac atatagtgtc aaatacggcc attcacatga tttaaaaata   46680
actataattt gatacgttta ttataacata attcacaaaa ttttgtcaac gttttatttt   46740
tacattattt tccggaagat tttccgcata tactccccat ataaaattat ataattatta   46800
atgtatacta tattactata ttaatttatg aaataaatta tatagtatat agtatactta   46860
tattacatat atataagggt ggtaactctg atatgccttc tatatcacat tattactaat   46920
atagagccta gtcaatttca aaactgatat ctcacatatc agaataaaaa agtattggct   46980
ttaataggca tatcagttac tagattttc ttaatttaga tccaacagga aggcaagcta   47040
agaatagaga gtctgctaag tctggagaat gtagtcctct tttcttcatt tcatccttac   47100
tctccagctt tatttgacct ttggagttga atactttaaa ctttctggta gtcaattctc   47160
ccacaagatc tgtattatcc ggtagtctta actcatcatc ctccagtaat tccttaacta   47220
cagaggctat atatgtggtt gtatcataat aaaaggcata agcctgggac cccctcttta   47280
gtggcatacc aaacttacat ggtactacct tcaaccagtc cagttttct tcaagtttta    47340
tctcttttaa tctatcagtt actcccccac ctacaccagt gtcgtctatt ttcacaacta   47400
ccgctagttt agggaactca ccatgtagag atttagcc                           47438
```